(12) United States Patent
Coroneo

(10) Patent No.: US 11,679,167 B2
(45) Date of Patent: Jun. 20, 2023

(54) OPHTHALMIC COMPOSITIONS, AND OCULAR USES THEREOF, OF INDIGO CARMINE

(71) Applicant: Minas Theodore Coroneo, Vaucluse (AU)

(72) Inventor: Minas Theodore Coroneo, Vaucluse (AU)

( * ) Notice: Subject to any disclaimer, the term of this patent is extended or adjusted under 35 U.S.C. 154(b) by 324 days.

(21) Appl. No.: 16/980,547

(22) PCT Filed: Mar. 15, 2019

(86) PCT No.: PCT/AU2019/050232
§ 371 (c)(1),
(2) Date: Sep. 14, 2020

(87) PCT Pub. No.: WO2019/173877
PCT Pub. Date: Sep. 19, 2019

(65) Prior Publication Data
US 2021/0000979 A1    Jan. 7, 2021

Related U.S. Application Data

(60) Provisional application No. 62/644,176, filed on Mar. 16, 2018.

(51) Int. Cl.
*A61K 49/00*   (2006.01)
*A61K 9/00*    (2006.01)

(52) U.S. Cl.
CPC .......... *A61K 49/006* (2013.01); *A61K 9/0048* (2013.01); *A61K 49/0023* (2013.01); *A61K 49/0034* (2013.01); *A61K 49/0043* (2013.01); *A61K 49/0071* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 7,014,991 | B2 | 3/2006 | Buono |
| 10,029,797 | B2 | 7/2018 | Space et al. |
| 10,993,909 | B1 | 5/2021 | Mousa |
| 2003/0096334 | A1 | 5/2003 | Buono |
| 2003/0232592 | A1 | 12/2003 | Lin |
| 2005/0283108 | A1 | 12/2005 | Savage |
| 2006/0081726 | A1 | 4/2006 | Gerondale |
| 2008/0082078 | A1 | 4/2008 | Berlin |
| 2009/0025716 | A1 | 1/2009 | Glazman |
| 2011/0290752 | A1 | 1/2011 | Yeager et al. |
| 2012/0251458 | A1 | 10/2012 | De Sousa Martins et al. |
| 2013/0118506 | A1 | 5/2013 | Osipov et al. |
| 2014/0102442 | A1 | 4/2014 | Wilson |
| 2014/0249463 | A1 | 9/2014 | Wardle et al. |
| 2018/0092775 | A1 | 4/2018 | de Juan et al. |
| 2018/0325731 | A1 | 11/2018 | Gross |

FOREIGN PATENT DOCUMENTS

| | | |
|---|---|---|
| AU | 2015202819 | 6/2015 |
| CN | 1112978328 | 6/2020 |
| CN | 111419787 | 7/2020 |
| JP | H1028696 A | 2/1998 |
| RU | 2131234 C1 | 6/1999 |
| WO | WO2004/082541 | 9/2004 |
| WO | WO 2010/105005 | 9/2010 |
| WO | WO 2019/173877 | 9/2019 |

OTHER PUBLICATIONS

Luke et al. Retinal tolerance to dyes. 2005 British Journal of Ophthalmology 89: 1188-1191. (Year: 2005).*
International Search Report dated May 31, 2019 for PCT/AU2019/050232.
Written Opinion dated May 31, 2019 for PCT/AU2019/050232.
Costa, E. et al. "Vital Dyes and Light Sources for Chromovitrectomy: Comparative Assessment of Osmolarity, pH, and Spectrophotometry," *Investigative Ophthalmology & Visual Science* (2009) 50:1, 385-391.
Rodrigues, E.B. et al. "Preclinical Investigation of the Retinal Biocompatibility of Six Novel Vital Dyes for Chromovitrectomy," *Retina: The Journal of Retinal and Vitreous Diseases* (2009) 29:4, 497-510.
Australian Government Department of Health, "COVID-19 Treatments" Jun. 1, 2021, Internet: https://www.health.gov.au/news/health-alerts/novel-coronavirus-2019-ncov-health-alert/>.
Berti et al. "Evaluation of Hydroxychloroquine-based Combination Therapies for the Treatment of COVID-19" *Open Forum Infectious Diseases*, vol. 7, No. SUPPL 1 (2020) S343 Abstract 556.
ClinicalTrials.Gov, "Proflaxis for Healthcare Professionals Using Hydroxychloroquine Plus Vitamin Combining Vitamins C, D and Zinc During COVID-19 Pandemia: An Observational Study," Identifier: NCT04326725, Available from the Internet: https://clinicaltrials.gov/ct2/history/NCT043267257V_1-View#StudyPageTop>, Published Mar. 27, 2020 according to ClinicalTrials.gov, Last Retrieved Jun. 8, 2021.
Korman, Tony M. "Favipiravir and the Need for Early Ambulatory Treatment of COVID-19" Antimicrobial Agents and Chemotherapy, 65:3 (2021) Article e02489-20, 2 pages.
Nickie Louise, "Dr. Vladimir Zelenko provides important update on three drug regimen of Hydroxychloroquine Sulfate, Zinc and Azithromycin (Z-Pak) he used to effectively treat 699 coronavirus patients with 100% success [Update 3]", Available from the Internet, <URL: https://techstartups.com/2020/03/31/dr-v ladimir-zelenko-providesimportant-update-three-drug-regimen-hydroxychloroquine-sulfate-zinc-azithromycin-zpak-used-effectively-treat-699-coronavirus-patients-1 00-su/>, Published Mar. 31, 2020 according to TechStartups.com, Last Retrieved Jun. 8, 2021.

(Continued)

*Primary Examiner* — Jennifer Lamberski
(74) *Attorney, Agent, or Firm* — Jones Day

(57) ABSTRACT

An ophthalmic composition comprising Indigo Carmine, or Indigo Carmine and Trypan Blue, for identification of intraocular structures and membranes within the eye, and methods of delivering and using the same, for surgical treatments of the eye, including glaucoma and cataract surgery.

24 Claims, 9 Drawing Sheets

(56) References Cited

OTHER PUBLICATIONS

Parker, Jack S. et al. "Trypan Blue-Assisted Microinvasive Glaucoma Surgery," *Journal Cataract and Refractive Surgery*, 43:12 (Jan. 12, 2018) p. 1613.
Rexam "A Clear Vision for Eyecare" XP055752773, Jun. 30, 2011, Retrieved from the Internet: http://www.lap.gr/files/pdf/REXAM_EYE_CARE.pdf [Retrieved Nov. 20, 2020].
Savarino et al. "Potential Therapies for Coronaviruses," *Expert Opinion on Therapeutics Patents*, 16:9 (2006) 1269-1288.
Xue et al. "Chloroquine is a Zinc Ionophore," *PLOS One*, 9:10 (2014) Article e109180, 6 pages.
Yoshikawa, Keiji et al. "Influence of Container Structures and Content Solutions on Dispensing Time of Ophthalmic Solutions," *Clinical Ophthalmology*, vol. 4 (Jan. 1, 2010) 481-486.

\* cited by examiner

OPHTHALMIC COMPOSITIONS, AND OCULAR USES THEREOF, OF INDIGO CARMINE

CROSS REFERENCE

This application is the National Phase application of International Application No. PCT/AU2019/050232, filed Mar. 15, 2019, which designates the United States and was published in English, and which claims the benefit of priority from U.S. Provisional Application No. 62/644,176, filed Mar. 16, 2018. The foregoing related applications, in their entirety, are incorporated herein by reference.

In addition, each of the references identified herein, in their entirety, are incorporated herein by reference.

TECHNICAL FIELD

This relates to ophthalmic compositions comprising Indigo Carmine or Indigo Carmine and Trypan Blue, and methods of delivering and using the same, particularly methods of using the same during ocular surgical procedures, such as during surgical procedures to treat patients suffering from glaucoma and/or cataract.

BACKGROUND

Glaucoma is an eye disease in which inappropriate pressure (usually elevated) damages retinal ganglion cells, resulting in permanent loss of field of vision. Left untreated, glaucoma can result in blindness, since the peripheral field of vision is lost initially and care is not typically sought until late in the course of the disease, when the more central field of vision is affected. Underlying this loss of visual field is the largely irreversible loss of retinal ganglion cells which apoptose in response to pressure (see, e.g., Tan, J. C., et al., "Mechanosensitivity and the eye: cells coping with the pressure", Br. J. Ophthalmol., 2006; 90:383-388).

The eye, arguably the most sophisticated "camera" that has ever evolved, is a pressurized organ, and the possible reasons for this include that it has an optical system that must remain precisely aligned despite very rapid eye movements. This optical system includes the cornea anteriorly and the crystalline lens suspended by zonular fibers from the ciliary body complex and in close relation to a diaphragm, the iris in which the pupil, of varying diameter, is located. This dual, anterior lens system is designed to focus light onto the "film plane" of the eye, the photosensitive retina. These optical components must maintain shape and alignment and position in order for a clear image to be formed. Since the eye is subjected to many movements (a "roving eye" effect, coordinated, since both eyes must move in unison for stereoscopic vision) and also to make up for the fact that since the human eye is compact and without compound optics (as in the fly), our field of vision, essential for survival, can be greatly increased by rapidly surveying a scene with eye movements. These eye movements include saccades which represent the fastest movement in the body with angular speeds of about 900°/s (see, e.g., Kandel, E. R., et al., Principles of Neural Science, McGraw Hill, 2000, 510, 784-786). If the eye were not pressurized, it would be impossible to maintain the position of these optical components without some "wobble" effect. Furthermore, some cell membrane transport mechanisms are dependent on pressure gradients, which need to be maintained to sustain normal function (see, e.g., Brenner, B. M., et al., "Transport of Molecules across Renal Glomerular Capillaries", Physiol. Rev., 1976, 6:502-534).

Fluid, also referred to as the aqueous humor, is continuously produced inside the eye by the epithelium of the ciliary body, thereby generating pressure as well as providing nutrients and removing waste products from the anterior eye. This fluid leaves the eye by a number of pathways. One fluid exit pathway, the so-called conventional drainage pathway, involves drainage of fluid from the inner eye (where ostensibly the bulk of aqueous humor resides) exiting the eye via the angle between the cornea and the iris (FIG. 1A). In this angle exists the trabecular meshwork (see, e.g., U.S. Pat. No. 6,372,449; Carreon, T., et al., "Aqueous outflow— A continuum from trabecular meshwork to episcleral veins", Prog. Retin. Eye Res., 2017, 57:108-133; Johnson, M., et al., "Unconventional aqueous humor outflow: A review", Exp. Eye Res., 2017, 158:94-111; and Carreon, T. A., et al., "Segmental outflow of aqueous humor in mouse and human", Exp. Eye Res., 2017, 158:59-66), through which fluid filters into the canal of Schlemm (a circumferential channel), thence into the deep scleral plexus and collector channels, and exiting outside the eye into episcleral/aqueous veins on the surface of the sclera (FIGS. 1A and 1B). Since this structural system involved in the conventional drainage pathway (including the trabecular meshwork, canal of Schlemm, deep scleral plexus, collector channels, and episcleral/aqueous veins) is thought to be the main controlling mechanism of fluid egress, responsible for maintaining eye pressure within a relatively narrow range for the life of the individual, it represents the most sophisticated valve in the body. Yet the function of this structural system is poorly understood and attempts to replace or subvert it are at the core of all glaucoma surgery, a branch of eye surgery that has had limited long-term success. A second fluid exit pathway, the uveoscleral or unconventional pathway, also includes passage via cornea, iris and retina (see, e.g., Carreon, T., et al., "Aqueous outflow—A continuum from trabecular meshwork to episcleral veins", Prog. Retin. Eye Res., 2017, 57:108-133). Fluid exits the posterior aspect of the uveal meshwork, passing through the ciliary muscle, and entering the suprachoroidal space. This pathway is variously estimated to account for 14-54% of outflow in human eyes and is also reduced in glaucoma. Another fluid exit pathway involves pumping fluid out of the eye by the retinal pigment epithelium (see, e.g., Pederson, J. E. et al., "Experimental retinal detachment: V. Fluid movement through the retinal hole", Arch. Ophthalmol., 1984, 102:136-139), but the relative importance of this pathway is thought to be small.

The cause of elevated pressure in glaucoma (and with increasing age) is not fully understood but is thought to involve a blockage (actual physical obstruction, pathophysiological and molecular changes or a combination) in the pathways that allow fluid outflow from the eye. Specific causes of this impediment remain elusive despite rigorous investigation (see, e.g., Coroneo, M. T., et al., "Electrical and morphological evidence for heterogeneous populations of cultured bovine trabecular meshwork cells", Exp. Eye Res., 1991, 52:375-88). An early notion was of "silting" of the valve with an increase in the amount and change in nature of extracellular material in the spaces of the endothelial meshwork (or juxtacanalicular tissue (JCT))—where the drainage route is most tortuous, then considered the probable site at which abnormally elevated resistance develops in early primary open angle glaucoma (see, e.g., Watson, P. G., et al., "The place of trabeculectomy in the treatment of glaucoma", Ophthalmology, 1981, 88:175-96). Increased cellularity and hyalinization in this region have also been noted. Subsequent studies in glaucomatous eyes found decreased Schlemm's canal cross-sectional area, perimeter and length and histopathologic changes in the outer wall of Schlemm's canal including increased collapse and narrowing of collector channels and intrascleral veins along with adhesion of Schlemm's canal endothelium to collector channels orifice walls and herniation of juxtacanalicular tissue with blockage of collector channel orifices (see, e.g., Hann, C. R., et al., "Anatomic changes in Schlemm's canal and collector channels in normal and primary open-angle glaucoma eyes using low and high perfusion pressures", Invest Ophthalmol. Vis. Sci., 2014 Aug. 19, 55(9):5834-41). This is consistent with the finding that the distal portion of the conventional outflow pathway is responsible for nearly 50% of outflow resistance in low-pressure perfused eyes and about 30% under higher pressures (Id.). A continuum model (FIG. 1B) of ocular outflow resistance in which integrated pathology encompassing the trabecular meshwork, Schlemm's canal, collector channels and distal outflow regions has been proposed (see, e.g., Carreon, T., et al., "Aqueous outflow—A continuum from trabecular meshwork to episcleral veins", Prog. Retin. Eye Res., 2017, 57:108-133). In this continuum model, reduced or altered trabecular meshwork mechanotransduction occurs due to alteration of soluble mechanosensing molecules or to their deposition. Mechanosensing occurs in the solution phase in the extracellular matrix and mechanotransduction on the cell surface by various channels. Basement membrane degradation is impaired in the trabecular meshwork and Schlemm's canal resulting in the lack of generation of pro- and anti-angiogenic molecules, including certain types of collagen fragments. Downstream, reduced collector channel frequency and/or dimension are observed. The fine regulation of degraded basement membrane protein fragments may be involved in regulation of collector channels and beyond.

Another important factor that may play a role in ocular surgical planning is that aqueous outflow is not uniform but is segmental around the circumference of the drainage angle. Preferential outflow occurs in the nasal and inferior quadrants of the eye (see, e.g., Cha, E. D., et al., "Variations in active outflow along the trabecular outflow pathway", Exp. Eye Res., 2016, 146:354-60), areas associated with more expanded trabecular meshwork and higher number of collector channels. Accordingly, circumferential flow around Schlemm's canal may be limited as aqueous flow through the trabecular meshwork and Schlemm's canal may be diverted into areas where the collector channels are most abundant to create this segmental flow pattern (FIG. 1B). These segmental variations in outflow facility may be of critical importance in the placement of stents that are inserted in the canal of Sclemm, since placement in the areas of maximum collector channel density will result in improved outflow.

To date, the only proven effective treatment for glaucoma is the lowering of intraocular pressure, which can be achieved pharmacologically, with laser treatment, or with surgery. Until recently, glaucoma surgery has provided variable results, and despite the fact that pressure can be lowered, it is not without risk as sight both visual and/or field of vision) may be reduced by the consequences of the surgery. Glaucoma surgery can be associated with astigmatism, corneal damage, cataract and retinal complications. So while the long-term aim is to protect the optic nerve by lowering pressure, in the short term, vision can be worse as a result of the surgery. Accordingly, these unwanted complications and consequences have required a solution that involves more effective surgery.

In recent years, minimally invasive surgery techniques has revolutionized glaucoma management (see, e.g., U.S. Pat. No. 7,291,125; and Coroneo, M. T., "Suprachoroidal Drainage—Centenarian Progress: An Inventor's Perspective", Francis, B. A., Sarkisian, S., and Tan, J., Editors, Minimally Invasive Glaucoma Surgery: the Science and the Practice. Thieme, New York, 2016). Minimally invasive surgery for glaucoma, also known as minimally invasive glaucoma surgery (MIGS), has borrowed from the techniques used in modern cataract surgery, in particular the use of small incisions and injectable implants or devices. The design and positioning of these implants or devices has depended on the prevailing view of the major sites of obstruction to aqueous outflow and given the lack of consensus, it is not surprising that different stent designs and techniques have been developed. Broadly, these devices are designed to:

1. bypass trabecular meshwork (stents are typically placed in the canal of Schlemm);
2. bypass the entire conventional drainage system by either:
   a. drainage into the suprachoroidal space (FIG. 1A); or
   b. drainage through the anterior chamber angle, through the wall of the eye and into the subconjunctival space; and/or
3. treat the canal of Schlemm and downstream structures by cannulation and injection of devices, such as ophthalmic viscosurgical devices or drugs.

During the implantation or insertion of these devices, it is helpful to be able to visualize structures in the angle, particularly the trabecular meshwork and the canal of Schlemm. Also, particularly for procedures in which implants are placed in the canal of Schlemm, it would be useful to know the sites of the best downstream drainage in the collector channels, and subsequently, the aqueous veins. This would allow optimal stent placement to take advantage of the downstream pathways of least resistance. This is particularly so because of the known variation in the numbers of collector channels according to location in relation to the 360 degrees of the conventional drainage angle.

Identification of membranes within the eye, whether pathogenic in origin, or those normally found within the eye, is difficult due to the transparent nature of such membranes. As such, these membranes cannot be readily visualized, and the diagnosis and treatment of various conditions associated with ocular membranes is hampered. Structures within the eye, such as the trabecular meshwork and the canal of Schlemm, both of which may be implicated in glaucoma, are difficult to visualize, again due to their relatively transparent nature or lack of pigmentation. Accordingly, a physician or surgeon diagnosing or treating conditions associated with membranes in the eye, with eye structures, or believed to be associated with structures of the eye is hampered by the inability to properly visualize such structures.

Moreover, existing methods of judging location and patency of outflow pathways are not well developed and are either inconsistent or impractical intra-operatively. Immediately after stent placement, lowering intraocular pressure via a paracentesis (small incision through the cornea and into the anterior chamber of the eye) can result in retrograde blood filling of Schlemm's canal (see, e.g., Wirbelauer, C., et al., "Role of Intraoperative Indirect Channelography in Glaucoma Stent Implantation", Klin. Monbl. Augenheilkd., 2017, 234:1378-1386), however judging this through 360 degrees of the angle during a surgical procedure is currently difficult with available imaging systems. And while the technique of using aqueous humor angiography, in conjunction with the dye indocyanine green, was able to confirm the segmental nature of drainage (see, e.g., Huang, A. S., et al., "Aqueous Angiography: Aqueous Humor Outflow Imaging in Live Human Subjects", Ophthalmology, 2017, 124:1249-1251), this and other techniques require special imaging equipment (see, e.g., Saraswathy, S., et al., "Aqueous Angiography: Real-Time and Physiologic Aqueous Humor Outflow Imaging", PLoS One, 2016 Jan. 25, 11(1): e0147176), thereby limiting their accessibility for routine surgery. The disadvantageous necessity of requiring the use of special imaging equipment for such techniques is presumably because of the limited visibility of the dye as it passes through the drainage system. Additionally, in contrast to acidic dyes, which are generally less toxic in tissue interactions (see, e.g., Grant, W. M. et al., Toxicology of the Eye, 4th ed., Springfield, Ill.: Charles C. Thomas, 1993), indocyanine green has the further disadvantage of being a basic dye, thus its use raises concerns of causing further tissue damage.

Another ophthalmic dye, Trypan Blue, while it has been demonstrated to be effective in identifying and visualizing ocular structures, particularly the anterior lens capsule and the trabecular meshwork (see, e.g., U.S. Pat. No. 6,372,449), it is not effective in identifying or visualizing the canal of Schlemm.

Developments in glaucoma and cataract surgery, as noted above, as well as corneal surgery, have necessitated the development of improved imaging techniques in order to obtain improved outcomes. In particular, there is a need for novel ophthalmic dye compositions, and techniques and procedures of using the same, to improve the effectiveness of minimally invasive glaucoma surgery (MIGS), cataract surgery, corneal surgery, including endothelial keratoplasty and small incision lenticule extraction (SMILE), a corneal refractive procedure (see, e.g., Shah, R., et al., "Results of small incision lenticule extraction: all-in-one femtosecond laser refractive surgery", J. Cataract Refract. Surg., 2011, 37:127-137), combinations of these procedures, and ocular surface diagnostic techniques. Additionally, since cataract and glaucoma can frequently coexist, surgical procedures that address glaucoma can often be carried out in conjunction with (usually following in serial fashion) cataract surgery (see, e.g., Rabin, R. L., et al., "Co-management of cataract and glaucoma in the era of minimally invasive glaucoma surgery", Curr. Opin. Ophthalmol., 2018, 29:88-95). For this reason, an ophthalmic dye composition, and technique and procedure of using the same, that facilitates both cataract and glaucoma surgery, or specific glaucoma surgical operations, would be very useful.

Accordingly, there is a need for an ophthalmic composition, and methods of delivering and using the same, for effectively visualizing and identifying structures within the eye, particularly ocular structures involved in fluid exit pathways, such as the trabecular meshwork and the canal of Schlemm, and to facilitate diagnosis and surgery, such as glaucoma surgery, minimally invasive glaucoma surgery (MIGS), cataract surgery, cataract and glaucoma surgery, corneal surgery, including endothelial keratoplasty and small incision lenticule extraction (SMILE), corneal refractive procedures, and to facilitate the placement of implants or devices (such as stents) to effect fluid flow.

DEFINITIONS

Terms are used herein as generally used in the art, unless otherwise defined in the following:

The term "ophthalmic device" is understood to refer to an object that is placed on or resides in the eye. The device may provide facilitated fluid (aqueous humor) flow. An ophthalmic device includes, but is not limited to, a stent, or an intraocular lens during cataract surgery.

SUMMARY

Some embodiments described herein may provide ophthalmic compositions, and methods of using the same, to identify, mark, or stain an intraocular structure(s) or membrane(s), and/or to treat an ocular disease or condition, such as glaucoma or a cataract.

In one aspect, provided herein is an ophthalmic composition, comprising Indigo Carmine.

In another aspect, provided herein is an ophthalmic composition, comprising Indigo Carmine and Trypan Blue.

In another aspect, provided herein is a method of ocular surgery in a patient in need thereof, comprising instilling an ophthalmic composition comprising Indigo Carmine into the patient's eye.

In another aspect, provided herein is a method of ocular surgery in a patient in need thereof, comprising instilling an ophthalmic composition comprising Indigo Carmine and Trypan Blue into the patient's eye.

In another aspect, provided herein is a method of ocular surgery in a patient in need thereof, comprising: instilling an ophthalmic composition comprising Indigo Carmine and an ophthalmic composition comprising Trypan Blue into the patient's eye.

In another aspect, provided herein is a method of identifying an intraocular structure(s) or membrane(s) within an eye of a patient in need thereof, comprising instilling an ophthalmic composition comprising Indigo Carmine into the patient's eye.

In another aspect, provided herein is a method of identifying an intraocular structure(s) or membrane(s) within an eye of a patient in need thereof, comprising instilling an ophthalmic composition comprising Indigo Carmine and Trypan Blue into the patient's eye.

In another aspect, provided herein is a method of identifying an intraocular structure(s) or membrane(s) within an eye of a patient in need thereof, comprising: instilling an ophthalmic composition comprising Indigo Carmine and an ophthalmic composition comprising Trypan Blue into the patient's eye.

In another aspect, provided herein is a method of introducing an ophthalmic device into an eye of a patient in need thereof, comprising:
  i) instilling an ophthalmic composition comprising Indigo Carmine into the patient's eye; and
  ii) introducing the ophthalmic device into the instilled eye.

In another aspect, provided herein is a method of introducing an ophthalmic device into an eye of a patient in need thereof, comprising:
  i) instilling an ophthalmic composition comprising Indigo Carmine and Trypan Blue into the patient's eye; and
  ii) introducing the ophthalmic device into the instilled eye.

In another aspect, provided herein is a method of introducing an ophthalmic device into an eye of a patient in need thereof, comprising:
  i) instilling an ophthalmic composition comprising Indigo Carmine and an ophthalmic composition comprising Trypan Blue into the patient's eye; and ii) introducing the ophthalmic device into the instilled eye.

In another aspect, provided herein is a method of identification of canal of Schlemm within an eye of a patient in need thereof, comprising instilling an ophthalmic composition comprising Indigo Carmine the patient's eye.

In another aspect, provided herein is a method of identification of canal of Schlemm within an eye of a patient in need thereof, comprising instilling an ophthalmic composition comprising Indigo Carmine and Trypan Blue the patient's eye.

In another aspect, provided herein is a method of identification of canal of Schlemm within an eye of a patient in need thereof, comprising instilling an ophthalmic composition comprising Indigo Carmine and an ophthalmic composition comprising Trypan Blue into the patient's eye.

In another aspect, provided herein is a method of cataract extraction and treatment of glaucoma in an eye of a patient in need thereof, comprising:
i) instilling an ophthalmic composition comprising Trypan Blue into the patient's eye;
ii) surgically extracting the cataract of the Trypan Blue instilled eye;
iii) instilling an ophthalmic composition comprising Indigo Carmine into the cataract extracted eye; and
iv) surgically treating the glaucoma of the Indigo Carmine instilled eye.

In another aspect, provided herein is a method of cataract extraction and treatment of glaucoma in an eye of a patient in need thereof, comprising:
i) instilling an ophthalmic composition comprising Indigo Carmine into the patient's eye;
ii) surgically extracting the cataract of the instilled eye; and
iii) surgically treating the glaucoma of the cataract extracted eye.

In another aspect, provided herein is a method of cataract extraction and treatment of glaucoma in an eye of a patient in need thereof, comprising:
i) instilling an ophthalmic composition comprising Indigo Carmine and Trypan Blue into the patient's eye;
ii) surgically extracting the cataract of the instilled eye; and
iii) surgically treating the glaucoma of the cataract extracted eye.

In another aspect, provided herein is a method of cataract extraction and treatment of glaucoma in an eye of a patient in need thereof, comprising:
i) instilling an ophthalmic composition comprising Indigo Carmine and an ophthalmic composition comprising Trypan Blue into the patient's eye;
ii) surgically extracting the cataract of the instilled eye; and
iii) surgically treating the glaucoma of the cataract extracted eye.

In certain embodiments of the ophthalmic composition, or the method of using the same, as disclosed herein, the ophthalmic composition is an aqueous composition.

In certain embodiments of the ophthalmic composition, or the method of using the same, as disclosed herein, the Indigo Carmine is present in an amount in the range of between approximately 0.001-0.4 wt. %, relative to the ophthalmic composition.

In certain embodiments of the ophthalmic composition, the ophthalmic device, or the method of treating, disclosed herein, the ophthalmic composition further comprises Trypan Blue.

In certain embodiments of the ophthalmic composition, the ophthalmic device, or the method of treating, disclosed herein, the Trypan Blue is present in an amount in the range of between approximately 0.001-0.1 wt. %, relative to the ophthalmic composition.

In certain embodiments of the ophthalmic composition, the ophthalmic device, or the method of treating, disclosed herein, the Trypan Blue is present in an amount less than 0.1 wt. %, such as less than 0.05 wt. %, relative to the ophthalmic composition.

In certain embodiments of the ophthalmic composition, the ophthalmic device, or the method of treating, disclosed herein, the Indigo Carmine is present in an amount in the range of between approximately 0.001-0.4 wt. %, and the Trypan Blue is present in an amount in the range of between approximately 0.001-0.1 wt. %, such as between approximately 0.001-0.05 wt. % or between approximately 0.001-0.045 wt. %, relative to the ophthalmic composition.

In certain embodiments of the ophthalmic composition, the ophthalmic device, or the method of treating, disclosed herein, the ophthalmic composition further comprises another dye, such as Brilliant Blue, Patent Blue, Indocyanine Green, or Fluorescein In certain embodiments of the ophthalmic composition, the ophthalmic device, or the method of treating, disclosed herein, the ophthalmic composition is an injectable ophthalmic formulation.

In certain embodiments of the ophthalmic composition, the ophthalmic device, or the method of treating, disclosed herein, the ophthalmic composition further comprises one or more additional ophthalmically acceptable excipients and additives.

In certain embodiments of the ophthalmic composition, the ophthalmic device, or the method of treating, disclosed herein, the ophthalmic composition is used for application to an eye, such as via topical application or injection, for example, via injection into the anterior chamber of said eye.

In certain embodiments of the ophthalmic composition, the ophthalmic device, or the method of treating, disclosed herein, the eye is a glaucomatous eye and/or has a cataract.

In certain embodiments of the ophthalmic composition, the ophthalmic device, or the method of treating, disclosed herein, the method includes an ocular surgery, or the ocular surgery is, selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, and ocular surface diagnostic technique.

In certain embodiments of the ophthalmic composition, the ophthalmic device, or the method of treating, disclosed herein, the method, or the ocular surgery, includes a combination of two or more of the following ocular surgeries selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, and ocular surface diagnostic technique.

In certain embodiments of the ophthalmic composition, the ophthalmic device, or the method of treating, disclosed herein, the ocular surgery is glaucoma surgery, such as a minimally invasive glaucoma surgery (MIGS).

In certain embodiments of the ophthalmic composition, the ophthalmic device, or the method of treating, disclosed herein, the ocular surgery is a combination of glaucoma surgery and cataract surgery.

In certain embodiments of the ophthalmic composition, the ophthalmic device, or the method of treating, disclosed herein, the ocular surgery is a combination of minimally invasive glaucoma surgery (MIGS) and cataract surgery.

In certain embodiments of the ophthalmic composition, the ophthalmic device, or the method of treating, disclosed herein, the ocular surgery is a combination of minimally invasive glaucoma surgery (MIGS) and endothelial keratoplasty.

In certain embodiments of the ophthalmic composition, the ophthalmic device, or the method of treating, disclosed herein, the ocular surgery is a combination of endothelial keratoplasty and cataract surgery.

In certain embodiments of the ophthalmic composition, the ophthalmic device, or the method of treating, disclosed herein, the ophthalmic composition is instilled into the eye by a plurality of injections, such as instilled into the eye by a plurality of injections into the anterior chamber of the eye.

In certain embodiments of the ophthalmic composition, the ophthalmic device, or the method of treating, disclosed herein, the method identifies, marks, or stains an intraocular structure(s) or membrane(s) within the patient's eye in a visually identifiable manner, such in a visually identifiable manner easily visible by the naked eye of a surgeon.

In certain embodiments of the ophthalmic composition, the ophthalmic device, or the method of treating, disclosed herein, the identified, marked, or stained intraocular structure(s) or membrane(s) within the patient's eye is selected from a group consisting of: a fine vessel, an aqueous vein, an episcleral vein, a collector channel, a collector channel/aqueous/episcleral vein system, an aqueous drainage system, a conjunctival venous system, a deep scleral plexus, a deep scleral plexus visually identifiable once a conjunctiva is reflected away, a trabecular meshwork, a canal of Schlemm, a suprachoroidal space, a scleral spur, anterior capsule of a crystalline lens, cornea, lens capsule, a retinal membrane, a corneal endothelial membrane, and Descemet's membrane.

In certain embodiments of the ophthalmic composition, the ophthalmic device, or the method of treating, disclosed herein, the Indigo Carmine of the ophthalmic composition identifies, marks, or stains a trabecular meshwork and the canal of Schlemm in the patient's eye.

In certain embodiments of the ophthalmic composition, the ophthalmic device, or the method of treating, disclosed herein, the Indigo Carmine of the ophthalmic composition identifies, marks, or stains the canal of Schlemm more than a trabecular meshwork in the patient's eye.

In certain embodiments of the ophthalmic composition, the ophthalmic device, or the method of treating, disclosed herein, the Indigo Carmine of the ophthalmic composition identifies, marks, or stains the trabecular meshwork less than a canal of Schlemm in the patient's eye.

In certain embodiments of the ophthalmic composition, the ophthalmic device, or the method of treating, disclosed herein, the method facilitates diagnosis of the patient's eye, facilitates diagnosis of the intraocular structure(s) or membrane(s) within the patient's eye, facilitates an ocular surgeon's diagnosis of fluid flow and drainage of the patient's eye during the ocular surgery, facilitates treatment of the patient's eye, facilitates surgical treatment of the patient's eye, facilitates surgical treatment of the identified intraocular structure(s) or membrane(s) within the eye, and/or facilitates surgical removal of the identified intraocular structure(s) or membrane(s) within the eye.

In certain embodiments of the ophthalmic composition, the ophthalmic device, or the method of treating, disclosed herein, the method facilitates extracting a cataract and treating glaucoma.

In certain embodiments of the ophthalmic composition, the ophthalmic device, or the method of treating, disclosed herein, the instilled ophthalmic composition facilitates accurate and/or precise inserting, placement, positioning, repositioning, lifting, and/or removal, of an ophthalmic device within the patient's eye, such as proximate the identified intraocular structure(s) or membrane(s) within the patient's eye.

In certain embodiments of the ophthalmic composition, the ophthalmic device, or the method of treating, disclosed herein, the ophthalmic device is a stent.

In certain embodiments of the ophthalmic composition, the ophthalmic device, or the method of treating, disclosed herein, the method facilitates an ocular surgeon's determination of the type of stent to utilize during the ocular surgery and/or facilitates an ocular surgeon's placement of the stent during the ocular surgery.

In certain embodiments of the ophthalmic composition, the ophthalmic device, or the method of treating, disclosed herein, the ophthalmic device is a stent, such as a glaucoma stent or a suprachoroidal stent.

In certain embodiments of the ophthalmic composition, the ophthalmic device, or the method of treating, disclosed herein, the ophthalmic device is an intraocular lens during cataract surgery.

In certain embodiments of the ophthalmic composition, the ophthalmic device, or the method of treating, disclosed herein, the ophthalmic device is introduced proximate or into the canal of Schlemm of the patient's eye.

In certain embodiments of the ophthalmic composition, the ophthalmic device, or the method of treating, disclosed herein, the ophthalmic device is inserted into the suprachoroidal space of the patient's eye.

In certain embodiments of the ophthalmic composition, the ophthalmic device, or the method of treating, disclosed herein, the ophthalmic device is pre-treated prior to placement, such as pre-treated with Indigo Carmine and/or pre-treated with Trypan Blue.

In certain embodiments of the ophthalmic composition, the ophthalmic device, or the method of treating, disclosed herein, the method further comprises instilling an ophthalmic composition comprising Trypan Blue.

In certain embodiments of the ophthalmic composition, the ophthalmic device, or the method of treating, disclosed herein, the instilled the ophthalmic composition comprises both Indigo Carmine and Trypan Blue.

In certain embodiments of the ophthalmic composition, the ophthalmic device, or the method of treating, disclosed herein, the ophthalmic composition is instilled into the patient's eye over a period of time in the range of between 1 second to 2 minutes, such as over a period of at least 10 seconds, at least 20 seconds, at least 30 seconds, at least 45 seconds, at least 1 minute, or at least 1.5 minutes.

In certain embodiments of the ophthalmic composition, the ophthalmic device, or the method of treating, disclosed herein, the ophthalmic composition is instilled into the patient's eye over a period of time until the composition egresses from one or more channels in the patient's eye.

In certain embodiments of the ophthalmic composition, the ophthalmic device, or the method of treating, disclosed herein, a plurality of the instillations of the ophthalmic composition is conducted over a period of time until at least 25%, at least 50%, at least 75%, at least 90%, or at least 95%, of the canal of Schlemm is visually identifiable.

In certain embodiments of the ophthalmic composition, the ophthalmic device, or the method of treating, disclosed herein, the method results in reduced surgical manipulation, reduced tissue manipulation, and/or less severe adverse side effects, relative to an ocular surgery not using said ophthalmic composition.

Other features and advantages of the subject matter described herein will be apparent from the description and figures, and from the claims.

BRIEF DESCRIPTION OF THE DRAWINGS

Aspects of the embodiments described herein may be best understood from the following detailed description when read with the accompanying figures.

DETAILED DESCRIPTION

Figure 1A:
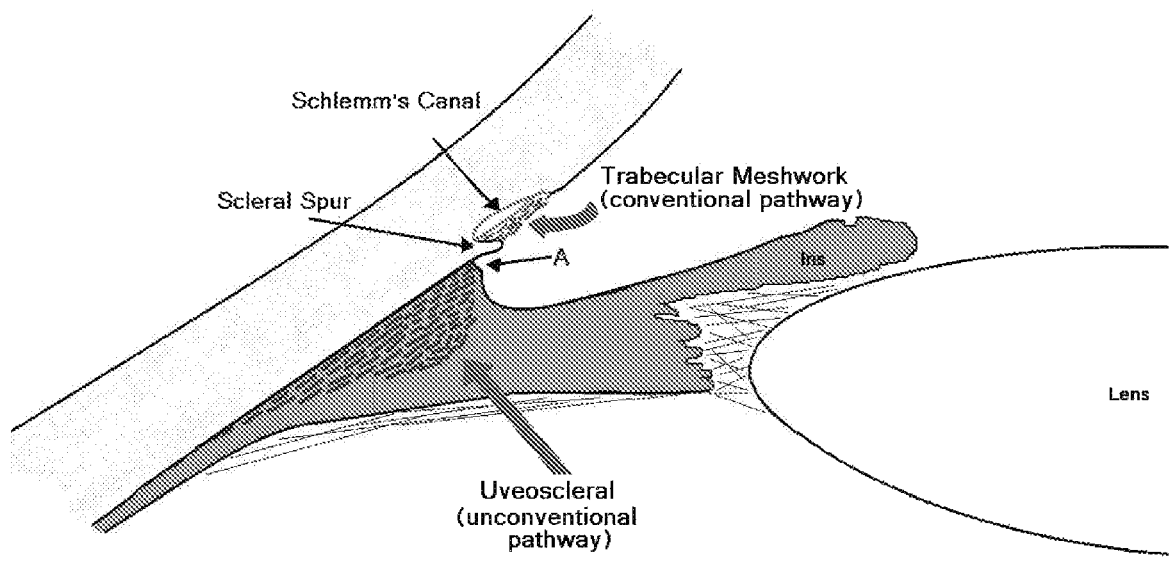
FIG. 1A is a schematic diagram of outflow pathways of the eye. illustrating locations of the trabecular (conventional) and uveoscleral (unconventional) aqueous humor outflow pathways. Arrow A points to the site of insertion of a suprachoroidal stent.
Figure 1B:
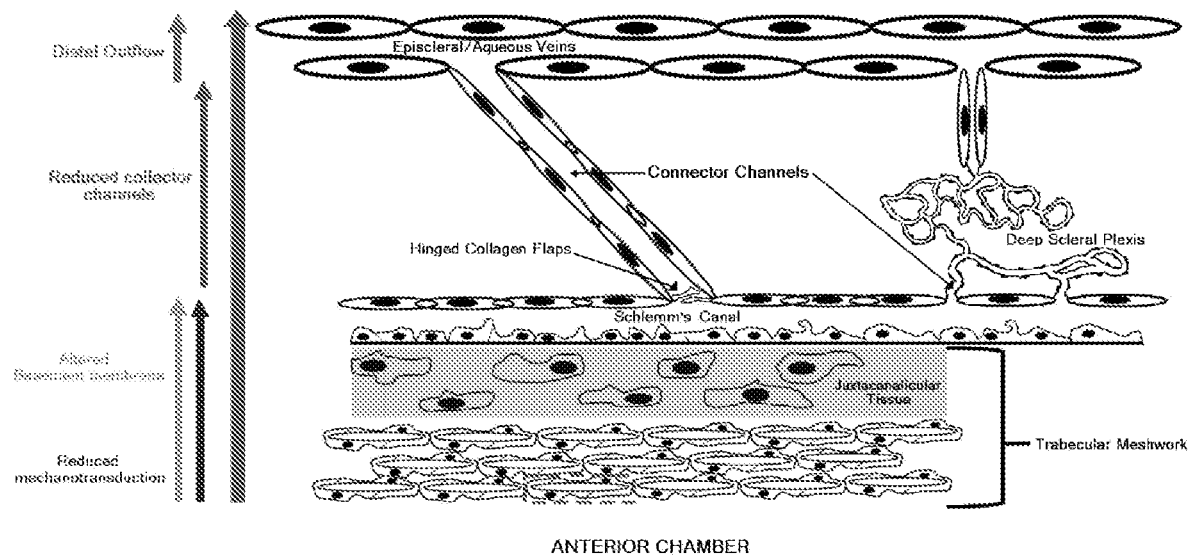
FIG. 1B is a schematic diagram of a proposed continuum model of outflow pathways of the eye (adapted from Carreon, T., et al., "Aqueous outflow—A continuum from trabecular meshwork to episcleral veins", Prog. Retin. Eye Res., 2017, 57:108-133). In this schematic diagram is illustrated a magnified, diagrammatic view of the anterior chamber angle, the trabecular meshwork and downstream (distal) pathways as labeled. The various components of the pathway act as a highly integrated organ system to control aqueous humor flow rather than as isolated regions. Reduced or altered mechanotransduction in the trabecular meshwork is due to alteration of soluble mechanosensing molecules or their deposition. At all levels, basement membrane degradation is impaired resulting in lack of generation of pro- and anti-angiogenic molecules and fragments of type IV collagen. Reduced collector channel frequency and/or dimension in the surrounding region of trabecular meshwork are observed. The fine regulation of degraded protein fragments of basement membrane may be involved in regulation of collector channels and distal flow regions.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Glaucoma is an eye disease in which inappropriate pressure (usually elevated) damages retinal ganglion cells, resulting in permanent loss of field of vision. Left untreated, glaucoma can result in blindness, since the peripheral field of vision is lost initially and care is not typically sought until late in the course of the disease, when the more central field of vision is affected. The present disclosure recognizes the importance of ophthalmic compositions, and methods of using the same, that can facilitate the ocular surgical procedures that may be utilized to treat glaucoma, as well as other diseases and/or conditions of the eye.

Indigo Carmine, also known as 5,5'-indigodisulfonic acid sodium salt or disodium 3,3'-dioxo-2,2'-bi-indolylidene-5,5'-disulfonate, is an acidic, anionic dye (see, e.g., Keng, C. S., et al., "Removal of cationic and anionic dyes by immobilized titanium dioxide loaded activated carbon", Malays. J. Anal. Sci., 2008, 12:451-457) that is derived from indigo by sulfonation, which renders the compound soluble in water. Indigo Carmine has been approved for use as a food colorant in the US and Europe (has the E number E132). Of critical importance is that Indigo Carmine exhibits low protein binding, which has been attributed to separation of its two sulfonic groups by 8 atoms (see, e.g., Tsopelas, C., et al., "Why certain dyes are useful for localizing the sentinel lymph node", J. Nucl. Med., 2002, 43:1377-82). Indigo Carmine is associated with a very low rate of both acute and chronic toxicity (see, e.g., Ferber, K. H., "Toxicology of indigo. A review", J. Environ. Pathol. Toxicol. Oncol., 1987, 7:73-83), and the few adverse reactions reported have been thought to have been idiosyncratic (see, e.g., Amchova, P., et al., "Health safety issues of synthetic food colorants", Regul. Toxicol. Pharmacol., 2015, 73:914-22). The dye has been used extensively in medicine across a broad range of specialties. For example, in urology, after intravenous injection, it is rapidly filtered by the kidneys and is useful highlighting portions of the urinary tract so that leaks can be detected (see, e.g., Luketic, L., et al., "Options to Evaluate Ureter Patency at Cystoscopy in a World Without Indigo Carmine", J. Minim. Invasive Gynecol., 2016, 23:878-85). The dye has also been extensively used in lymphatic mapping (see, e.g., Uhara, H., et al., "Sentinel lymph node biopsy in Japan", Int. J. Clin. Oncol., 2009, 14:490-6), detecting amniotic membrane rupture (see, e.g., Adekola, H., et al., "Outcomes following intra-amniotic instillation with indigo carmine to diagnose prelabor rupture of membranes in singleton pregnancies: a single center experience", J. Matern. Fetal Neonatal Med., 2016, 29:544-9), cerebrospinal fluid leakage (see, e.g., Kaufman, B., et al., "Acquired spontaneous, nontraumatic normal-pressure cerebrospinal fluid fistulas originating from the middle fossa", Radiology, 1977, 122:379-87) and to enhance detection of pathology during endoscopy (see, e.g., Brown, S. R., et al., "Chromoscopy versus conventional endoscopy for the detection of polyps in the colon and rectum", Cochrane Database Syst. Rev., 2016 Apr. 7, 4:CD006439).

The present application provides an ophthalmic composition comprising Indigo Carmine, or an ophthalmic composition comprising a combination of Indigo Carmine and Trypan Blue, for topical or ocular application, such as instillation by injection, and methods of using the same, such as for identification, marking, and/or staining of intraocular structures or membranes, and to facilitate ocular surgeries, such as glaucoma surgery and cataract surgery, among other ocular surgeries disclosed herein.

In certain embodiments, the ophthalmic composition may comprise or consist of a single dye, wherein the single dye is Indigo Carmine, or may comprise or consist of a combination of dyes, wherein the combination of dyes comprises Indigo Carmine and at least one dye selected from the group consisting of: Trypan Blue, Brilliant Blue, Patent Blue, Indocyanine Green, and Fluorescein. In certain embodiments, the combination of dyes is Indigo Carmine and Trypan Blue.

In certain embodiments, the Indigo Carmine contained within the ophthalmic composition disclosed herein may be present in low concentrations, for example, in an amount in the range of between approximately 0.001-0.4 wt. %, relative to the ophthalmic composition, such as present in an amount in the range of between approximately 0.001-0.3 wt. %, between approximately 0.001-0.2 wt. %, between approximately 0.001-0.1 wt. %, between approximately 0.001-0.05 wt. %, between approximately 0.001-0.01 wt. %, between approximately 0.004-0.4 wt. %, between approximately 0.004-0.04 wt. %, between approximately 0.005-0.4 wt. %, between approximately 0.005-0.3 wt. %, between approximately 0.005-0.2 wt. %, between approximately 0.005-0.1 wt. %, between approximately 0.005-0.05 wt. %, between approximately 0.005-0.01 wt. %, between approximately 0.01-0.35 wt. %, between approximately 0.01-0.3 wt. %, between approximately 0.01-0.25 wt. %, between approximately 0.01-0.2 wt. %, between approximately 0.01-0.15 wt. %, between approximately 0.01-0.1 wt. %, between approximately 0.04-0.4 wt. %, between approximately 0.05-0.4 wt. %, between approximately 0.1-0.4 wt. %, between approximately 0.15-0.4 wt. %, between approximately 0.2-0.4 wt. %, between approximately 0.25-0.4 wt. %, between approximately 0.3-0.4 wt. %, between approximately 0.35-0.4 wt. %, between approximately 0.1-0.3 wt. %, between approximately 0.1-0.2 wt. %, between approximately 0.01-0.05 wt. %, or between approximately 0.05-0.1 wt. %, relative to the ophthalmic composition. In certain embodiments, the Indigo Carmine may be present in the ophthalmic composition disclosed herein in an amount of approximately 0.001 wt. %, approximately 0.002 wt. %, approximately 0.003 wt. %, approximately 0.004 wt. %, approximately 0.005 wt. %, approximately 0.006 wt. %, approximately 0.007 wt. %, approximately 0.008 wt. %, approximately 0.009 wt. %, approximately 0.01 wt. %, approximately 0.02 wt. %, approximately 0.03 wt. %, approximately 0.04 wt. %, approximately 0.05 wt. %, approximately 0.06 wt. %, approximately 0.07 wt. %, approximately 0.08 wt. %, approximately 0.09 wt. %, approximately 0.1 wt. %, approximately 0.2 wt. %, approximately 0.3 wt. %, or approximately 0.4 wt. %, relative to the ophthalmic composition. In certain embodiments, the Indigo Carmine may be present in the ophthalmic composition disclosed herein in an amount of at least 0.001 wt. %, at least 0.002 wt. %, at least 0.003 wt. %, at least 0.004 wt. %, at least 0.005 wt. %, at least 0.006 wt. %, at least 0.007 wt. %, at least 0.008 wt. %, at least 0.009 wt. %, at least 0.01 wt. %, at least 0.02 wt. %, at least 0.03 wt. %, at least 0.04 wt. %, at least 0.05 wt. %, at least 0.06 wt. %, at least 0.07 wt. %, at least 0.08 wt. %, at least 0.09 wt. %, at least 0.1 wt. %, at least 0.15 wt. %, at least 0.2 wt. %, at least 0.25 wt. %, at least 0.3 wt. %, or at least 0.35 wt. %, relative to the ophthalmic composition.

In certain embodiments, when the ophthalmic composition comprises Indigo Carmine and Trypan Blue, or when an ophthalmic composition comprising Trypan Blue is co-administered with the ophthalmic composition comprising Indigo Carmine (such as at the same time, or sequentially before or after), the Trypan Blue may be present in an amount in the range of between approximately 0.001-0.1 wt. %, relative to the ophthalmic composition. In certain embodiments, when the ophthalmic composition comprises Indigo Carmine and Trypan Blue, or when an ophthalmic composition comprising Trypan Blue is co-administered with the ophthalmic composition comprising Indigo Carmine (such as at the same time, or sequentially before or after), the Trypan Blue may be present in an amount in the range of at least 0.001 wt. % and less than 0.1 wt. %, relative to the ophthalmic composition, for example, the Trypan Blue is present in an amount in the range of at least 0.001 wt. % and less than 0.05 wt. %, less than 0.04 wt. %, less than 0.03 wt. %, less than 0.02 wt. %, or less than 0.01 wt. %, relative to the ophthalmic composition. In certain embodiments, when the ophthalmic composition comprises Indigo Carmine and Trypan Blue, or when an ophthalmic composition comprising Trypan Blue is co-administered with the ophthalmic composition comprising Indigo Carmine (such as at the same time, or sequentially before or after), the Trypan Blue may be present in an amount in the range of between approximately 0.001-0.1 wt. %, for example, the Trypan Blue may be present in an amount in the range of between approximately 0.001-0.05 wt. %, such as between approximately 0.001-0.045 wt. %, between approximately 0.001-0.04 wt. %, between approximately 0.001-0.035 wt. %, between approximately 0.001-0.03 wt. %, between approximately 0.001-0.025 wt. %, between approximately 0.001-0.02 wt. %, between approximately 0.001-0.015 wt. %, between approximately 0.001-0.01 wt. %, between approximately 0.005-0.1 wt. %, between approximately 0.005-0.05 wt. %, between approximately 0.005-0.045 wt. %, between approximately 0.005-0.04 wt. %, between approximately 0.005-0.035 wt. %, between approximately 0.005-0.03 wt. %, between approximately 0.005-0.025 wt. %, between approximately 0.005-0.02 wt. %, between approximately 0.005-0.015 wt. %, between approximately 0.005-0.01 wt. %, between approximately 0.01-0.1 wt. %, between approximately 0.01-0.05 wt. %, between approximately 0.01-0.045 wt. %, between approximately 0.01-0.04 wt. %, between approximately 0.01-0.035 wt. %, between approximately 0.01-0.03 wt. %, between approximately 0.01-0.025 wt. %, between approximately 0.01-0.02 wt. %, between approximately 0.01-0.015 wt. %, or between approximately 0.02-0.04 wt. %, relative to the ophthalmic composition. In certain embodiments, when the ophthalmic composition comprises Indigo Carmine and Trypan Blue, or when an ophthalmic composition comprising Trypan Blue is co-administered with the ophthalmic composition comprising Indigo Carmine (such as at the same time, or sequentially before or after), the Trypan Blue may be present in an amount of approximately 0.001 wt. %, for example, the Trypan Blue may be present in an amount of approximately 0.005 wt. %, approximately 0.01 wt. %, approximately 0.015 wt. %, approximately 0.02 wt. %, approximately 0.025 wt. %, approximately 0.03 wt. %, approximately 0.035 wt. %, approximately 0.04 wt. %, approximately 0.045 wt. %, approximately 0.05 wt. %, or approximately 0.1 wt. %, relative to the ophthalmic composition.

In certain embodiments, the ophthalmic composition may comprise Indigo Carmine and Trypan Blue, or an ophthalmic composition comprising Indigo Carmine may be co-administered with an ophthalmic composition comprising Trypan Blue (such as at the same time, or sequentially before or after), wherein the Indigo Carmine is present in an amount in the range of between approximately 0.001-0.4 wt. %, and the Trypan Blue is present in an amount in the range of between approximately 0.001-0.1 wt. %, relative to the ophthalmic composition. For example, in certain embodiments, the ophthalmic composition may comprise the Indigo Carmine in an amount in the range of between approximately 0.005-0.3 wt. %, and the Trypan Blue in an amount in the range of between approximately 0.005-0.05 wt. %, relative to the ophthalmic composition, such as comprise the Indigo Carmine in an amount in the range of between approximately 0.005-0.3 wt. %, and the Trypan Blue in an amount in the range of between approximately 0.005-0.045 wt. %, relative to the ophthalmic composition; comprise the Indigo Carmine in an amount in the range of between approximately 0.005-0.3 wt. %, and the Trypan Blue in an amount in the range of between approximately 0.005-0.04 wt. %, relative to the ophthalmic composition; or comprise the Indigo Carmine in an amount of approximately 0.01 wt. %, and the Trypan Blue in an amount of approximately 0.01 wt. %, relative to the ophthalmic composition.

In certain embodiments, the ophthalmic composition disclosed herein is an aqueous composition, such as a sterile aqueous solution. In certain embodiments, the ophthalmic composition disclosed herein comprises or is an ophthalmic irrigation solution, wherein the ophthalmic composition is at physiological pH and comprises an isotonic salt concentration. For example, the ophthalmic irrigation solution may be a balanced salt solution (BSS), a Balanced Salt Solution Plus (BSS Plus®), an Alsever's salt solution, an Earle's balanced salt solution (EBSS), a Gey's balanced salt solution (GBSS), a Hanks' balanced salt solution (MSS), a Dulbecco's phosphate buffered saline (PBS), a Puck's balanced salt solution, a Ringer's balanced salt solution (RBSS), a Simm's balanced salt solution (SBSS), a TRIS-buffered saline (TBS), or a Tyrode's balanced salt solution solution (TBSS), or combinations thereof. For other examples of irrigation solutions, see, e.g., U.S. Pat. No. 4,550,022, or International Publication WO 1994/008602. In certain embodiments, the ophthalmic composition disclosed herein further comprises one or more additional ophthalmically acceptable excipients and additives. In certain embodiments, the ophthalmic composition disclosed herein further comprises sugar compounds, such as glucose or dextrose. In certain embodiments, the ophthalmic composition disclosed herein further comprises anti-oxidant compounds, such as glutathione. In certain embodiments, the ophthalmic composition disclosed herein is an isotonic, aqueous solution, such as an isotonic, sterile, aqueous solution, having a neutral pH (for example, between pH 6-8, such as between pH 6.5-7.5, between pH 7-7.6, between pH 7.3-7.6, or between pH 6.8-7.2, such as approximately pH 7), and may further comprise certain cations, such as sodium, potassium, calcium, and/or magnesium cations, and comprise certain anions, such as phosphate ion, mono-hydrogen phosphate ion, di-hydrogen phosphate ion, citrate ion, bicarbonate, or chloride ion, or combinations thereof. In certain embodiments, the ophthalmic composition may comprise inorganic salts and/or organic salts, such as sodium chloride, potassium chloride, calcium chloride, magnesium chloride, sodium acetate, sodium phosphate, sodium mono-hydrogen phosphate (sodium mono-hydrogen orthophosphate), sodium di-hydrogen phosphate (sodium di-hydrogen orthophosphate), sodium bicarbonate, or sodium citrate, or combinations thereof. In certain embodiments, the ophthalmic composition disclosed herein has an osmolality between 200-400 mosmol/kg, such as 250-350 mosmol/kg, 300-350 mosmol/kg, or 250-325 mosmol/kg, for example, 200 mosm/kg, 250 mosm/kg, 275 mosm/kg, 300 mosm/kg, or 325 mosm/kg, such as 300 mosm/kg. In certain embodiments, the ophthalmic composition comprising or consisting of Indigo Carmine, or Indigo Carmine and Trypan Blue, may further comprise one or more additional ophthalmically acceptable excipients and additives, comprising for example, carriers, stabilizers, osmolarity adjusting agent, a preservative, a buffer agent, or a tonicity adjusting agent, thickeners and other excipients.

In certain embodiments, the ophthalmic composition disclosed herein is suitable for application to an eye, for example, is suitable for instillation into the eye of patient in need thereof, such as instillation by injection or via topical application to said eye. In certain embodiments, the ophthalmic composition disclosed herein is an injectable ophthalmic composition. In certain embodiments, the ophthalmic composition disclosed herein is instilled by injection into eye, such as instilled by injection into the anterior chamber of said eye, for example, instilled by a plurality of injections into the anterior chamber of said eye.

In certain embodiments, the patient's eye has one or more ocular conditions or diseases. For example, the patient's eye may be a glaucomatous eye, and/or may have a cataract. In certain embodiments, the patient's eye requires ocular surgery. In certain embodiments, a method for ocular surgery in a patient in need thereof is provided, wherein said method comprises instilling the ophthalmic composition as disclosed herein. For example, in certain embodiments, the method includes an ocular surgery, or the ocular surgery is, selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, and ocular surface diagnostic technique. In certain embodiments, the method, or the ocular surgery, includes a combination of two or more of the following ocular surgeries selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, and ocular surface diagnostic technique. For example, the ocular surgery is or includes glaucoma surgery, such as minimally invasive glaucoma surgery (MIGS). In certain embodiments, the ocular surgery is or includes cataract surgery. In certain embodiments, the ocular surgery comprises extracting a cataract and treating glaucoma. In certain embodiments, the ocular surgery is or includes endothelial keratoplasty, such as Descemet's Membrane Endothelial Keratoplasty (DMEK). In certain embodiments, the ocular surgery is or includes capsulorhexis. In certain embodiments, the ocular surgery is or includes a small incision lenticule extraction (SMILE). In certain embodiments, the ocular surgery is or includes an Ab externo Canaloplasty (ABeC). In certain embodiments, the ocular surgery is a combination of glaucoma surgery and cataract surgery. In certain embodiments, the ocular surgery is a combination of minimally invasive glaucoma surgery (MIGS) and cataract surgery. In certain embodiments, the ocular surgery is a combination of minimally invasive glaucoma surgery (MIGS) and endothelial keratoplasty. In certain embodiments, the ocular surgery is a combination of endothelial keratoplasty and cataract surgery.

In certain embodiments, a patient for whom the ophthalmic composition disclosed herein, and methods of using the same, may be suitable for include, but are not limited to, a patient that has both cataract and glaucoma and is receiving topical medication to manage the glaucoma; an elderly patient, such as over the age of 40, over 50, over 60, over 70, or over 80 years of age; a patient that has an intraocular pressure control that is suboptimal, such as in an elderly patient; a patient, such as an elderly patient, that has dry eye syndrome. Dry eye syndrome is more common in elderly patient, and topical medication can exacerbate this condition, causing discomfort and reduced vision. Topical anti-glaucoma medications (such as beta blockers) can be absorbed systemically and can have significant (even fatal) side effects. The aim in treating such a patient is to restore sight by removing the cataract and to make the patient independent of topical drug use by surgically reducing eye pressure. As in a routine cataract extraction, a peripheral corneal incision may be made to enter the anterior chamber of the eye and the dye composition may then be instilled, initially to stain the anterior capsule of the cataractous lens—this can facilitate creation of an opening in the capsule (capsulorhexis) in order to gain access to the cataract, which may be removed by phacoemulsification. Following the phacoemulsification, an intraocular lens may be inserted to replace the dioptric power of the cataractous lens that has been removed. Following insertion of the intraocular lens, attention may then be turned to dealing with the glaucoma in the patient's eye. The ophthalmic composition containing Indigo Carmine, as disclosed herein, may be re-injected into the anterior chamber with the aim of delineating critical anatomical structures in the anterior chamber angle, such as Schlemm's canal. Furthermore, injection of the ophthalmic composition containing Indigo Carmine will provide information regarding the presence, location and numbers of collector channels that may exit the eye. This information can then be used to determine the type and location of the MIGS stent to be used to treat the glaucoma. For example, if collector channels are numerous in a particular quadrant of the eye, such as in two quadrants, then stents may be placed in the canal of Schlemm, underlying this area(s) of collector channel preponderance. If, for example, the collector channels are sparse, then a suprachoroidal stent may be used, thereby bypassing this path of resistance. Following insertion of the stent(s), the ophthalmic composition containing Indigo Carmine may be re-instilled to check patency of the stent and flow from the stent out into the aqueous veins or suprachoroidal space. In certain embodiments, the ophthalmic composition may contain Indigo Carmine and Trypan Blue, such as 0.001-0.4 wt. % of Indigo Carmine, for example, 0.1 wt. % of Indigo Carmine, and 0.001-0.1 wt. % of Trypan Blue, for example, 0.0125 wt. % of Trypan Blue, relative to the ophthalmic composition.

In certain embodiments, the methods as disclosed herein identifies, marks, or stains an intraocular structure(s) or membrane(s) within the patient's eye in a visually identifiable manner, for example, the method identifies, marks, or stains an intraocular structure(s) or membrane(s) within the patient's eye in a visually identifiable manner easily visible by the naked eye of a surgeon, and as a result, the method facilitates ready identification of the intraocular structure(s) or membrane(s) within the instilled eye. The method, in certain embodiments, may identify, mark, or stain, an intraocular structure(s) or membrane(s), or a plurality of intraocular structures or membranes, within the patient's eye in a visually identifiable manner. In certain embodiments, the ophthalmic composition, or the method, as disclosed herein, identifies, marks, or stains a portion of the intraocular structure(s) or membrane(s) within the patient's eye, or identifies, marks, or stains a plurality of the intraocular structures or membranes within the patient's eye.

In certain embodiments, the intraocular structure(s) or membrane(s) (or portions thereof) identified, marked, or stained, within the patient's eye by the ophthalmic composition, or the method, as disclosed herein, may be selected from a group consisting of: a fine vessel, an aqueous vein, an episcleral vein, a collector channel, a collector channel/aqueous/episcleral vein system, an aqueous drainage system, a conjunctival venous system, a deep scleral plexus, a deep scleral plexus visually identifiable once a conjunctiva is reflected away, a trabecular meshwork, a canal of Schlemm, a suprachoroidal space, a scleral spur, anterior capsule of a crystalline lens, cornea, lens capsule, a retinal membrane, a corneal endothelial membrane, and Descemet's membrane. In certain embodiments, the intraocular structure(s) or membrane(s) (or portions thereof) identified, marked, or stained, within the patient's eye by the ophthalmic composition, or the method, as disclosed herein, is a fine vessel. In certain embodiments, the identified, marked, or stained, intraocular structure(s) or membrane(s) (or portion thereof) is an aqueous vein. In certain embodiments, the identified, marked, or stained, intraocular structure or membrane (or portion thereof) an episcleral vein. In certain embodiments, the identified, marked, or stained, intraocular structure or membrane (or portion thereof) is a collector channel. In certain embodiments, the identified, marked, or stained, intraocular structure(s) or membrane(s) (or portion thereof) is a collector channel/aqueous/episcleral vein system. In certain embodiments, the identified, marked, or stained, intraocular structure(s) or membrane(s) (or portion thereof) is an aqueous drainage system of said eye, such as a conventional drainage system of said eye. In certain embodiments, the identified, marked, or stained, intraocular structure(s) or membrane(s) (or portion thereof) is a conjunctival venous system. In certain embodiments, the identified, marked, or stained, intraocular structure(s) or membrane(s) (or portion thereof) is a deep scleral plexus, such as a deep scleral plexus visually identifiable once the conjunctiva is reflected away. In certain embodiments, the identified, marked, or stained, intraocular structure(s) or membrane(s) (or portion thereof) is a trabecular meshwork, such as a posterior aspect of a trabecular meshwork. In certain embodiments, the identified, marked, or stained, intraocular structure(s) or membrane(s) (or portion thereof) is a canal of Schlemm. In certain embodiments, the identified, marked, or stained, intraocular structure(s) or membrane(s) (or portion thereof) is a suprachoroidal space. In certain embodiments, the identified, marked, or stained, intraocular structure(s) or membrane(s) (or portion thereof) is a scleral spur. In certain embodiments, the identified, marked, or stained, intraocular structure(s) or membrane(s) (or portion thereof) is the anterior capsule of a crystalline lens. In certain embodiments, the identified, marked, or stained, intraocular structure(s) or membrane(s) (or portion thereof) is a trabecular meshwork and a canal of Schlemm in the patient's eye. In certain embodiments, the Indigo Carmine of the ophthalmic composition identifies, marks, or stains a canal of Schlemm more than a trabecular meshwork in the patient's eye. In certain embodiments, the Indigo Carmine of the ophthalmic composition identifies, marks, or stains a trabecular meshwork less than a canal of Schlemm in the patient's eye.

In certain embodiments, the ophthalmic composition, or the method, as disclosed herein, facilitates diagnosis of the patient's eye. For example, the ophthalmic composition, or the method, as disclosed herein, facilitates diagnosis of the intraocular structure(s) or membrane(s) within the patient's eye, facilitates an ocular surgeon's diagnosis of fluid flow and drainage of the patient's eye during the ocular surgery, facilitates treatment of the patient's eye, facilitates surgical treatment of the patient's eye, facilitates surgical treatment of the identified intraocular structure(s) or membrane(s) within the eye, and/or facilitates surgical removal of the identified intraocular structure(s) or membrane(s) within the eye, such as facilitates extracting a cataract and treating glaucoma.

In certain embodiments, the methods, as disclosed herein, further comprises introducing an ophthalmic device into the instilled eye and/or the method facilitates the introducing of an ophthalmic device into the instilled eye, such as the Indigo Carmine instilled patient's eye or the Indigo Carmine and Trypan Blue instilled patient's eye. For example, the ophthalmic composition, or the method, as disclosed herein, facilitates accurate and/or precise inserting, placement, positioning, repositioning, lifting, and/or removal, of an ophthalmic device within the patient's eye, such as proximate the identified intraocular structure(s) or membrane(s) within the patient's eye. For example, in certain embodiments, the ophthalmic composition, or the method, as disclosed herein, facilitates accurate and/or precise inserting, placement, positioning, repositioning, lifting, and/or removal, of an ophthalmic device proximate to, or into, the canal of Schlemm of the patient's eye. For example, in certain embodiments, the ophthalmic composition, or the method, as disclosed herein, facilitates accurate and/or precise inserting, placement, positioning, repositioning, lifting, and/or removal, of an ophthalmic device proximate to, or into, the suprachoroidal space of the patient's eye.

In certain embodiments, the ophthalmic composition, or the method, as disclosed herein, facilitates an ocular surgeon's determination of the type of stent to utilize during the ocular surgery, facilitates an ocular surgeon's placement of the stent during the ocular surgery, or facilitates an ocular surgeon's determination of the type of stent to utilize and the placement of the stent during the ocular surgery. In certain embodiments, the ophthalmic device utilized in the methods, as disclosed herein, is a stent, such as a glaucoma stent or a suprachoroidal stent. In certain embodiments, the ophthalmic device may be pre-treated with Indigo Carmine and/or pre-treated with Trypan Blue.

In certain embodiments, the method as disclosed herein, further comprises instilling an ophthalmic composition comprising Trypan Blue. In certain embodiments, the method as disclosed herein, the instilled the ophthalmic composition comprises both Indigo Carmine and Trypan Blue.

In certain embodiments, the method as disclosed herein, intraocular structures or membranes of the instilled eye are identified, marked, or stained, by Indigo Carmine prior to extracting of the cataract. In certain embodiments, the method as disclosed herein, intraocular structures or membranes of the instilled eye are identified, marked, or stained, by both Indigo Carmine and Trypan Blue prior to extracting of the cataract.

In certain embodiments, the method as disclosed herein, surgical treatment of the patient's glaucoma in said Indigo Carmine instilled eye comprises introducing an ophthalmic device into said eye. For example, the method may comprise: a) visually identifying an Indigo Carmine stained canal of Schlemm; and b) introducing an ophthalmic device into the patient's eye proximate the Indigo Carmine stained canal of Schlemm.

In certain embodiments, according to the methods disclosed herein, the Indigo Carmine containing ophthalmic composition and the Trypan Blue containing ophthalmic composition are co-instilled concurrently. In certain embodiments, according to the methods disclosed herein, the Indigo Carmine containing ophthalmic composition and the Trypan Blue containing ophthalmic composition are co-instilled sequentially with instilling of the Indigo Carmine containing ophthalmic composition followed by the Trypan Blue containing ophthalmic composition. In certain embodiments, according to the methods disclosed herein, the Indigo Carmine containing ophthalmic composition and the Trypan Blue containing ophthalmic composition are co-instilled sequentially with instilling of the Trypan Blue containing ophthalmic composition followed by the Indigo Carmine containing ophthalmic composition.

In certain embodiments, the ophthalmic composition may be instilled into the patient's eye over a period of time in the range of between 1 second to 2 minutes, according to the methods as disclosed herein. For example, the ophthalmic composition may be instilled into the patient's eye over a period of time in the range of between 1 sec and 1.5 minutes, such as between 10 seconds and 1 minute, between 15 seconds and 2 minutes, between 30 seconds and 1 minute, or between 45 seconds and 1.5 minutes. For example, the ophthalmic composition may be instilled into the patient's eye over a period of at least 10 seconds, such as at least 20 seconds, at least 30 seconds, at least 45 seconds, at least 1 minute, or at least 1.5 minutes. In certain embodiments, the ophthalmic composition may be instilled into the patient's eye over a period of time until the composition egresses from one or more channels in the patient's eye. In certain embodiments, the ophthalmic composition may be instilled into the patient's eye via a plurality of instillations conducted over a period of time until at least 25% of the canal of Schlemm is visually identifiable, such as at least 50%, at least 75%, at least 90%, or at least 95%, of the canal of Schlemm is visually identifiable.

In certain embodiments, use of the ophthalmic composition according to the methods as disclosed herein, results in reduced surgical manipulation, reduced tissue manipulation, and/or less severe adverse side effects, relative to an ocular surgery not using said ophthalmic composition.

The technique Ab interno canaloplasty (ABiC) has been described as a treatment for glaucoma (see, e.g., U.S. Pat. Nos. 7,699,882; 7,967,772; 8,034,105; 8,172,830; 8,491,549; 8,894,603; 9,095,412; and 9,216,109). In this technique, an illuminated microcatheter is inserted into the anterior chamber via a small corneal incision and provides continual trans-scleral visualization of the catheter location within the canal of Schlemm. After catheterisation, the canal of Schlemm is "viscodilated" with an ophthalmic viscosurgical device. This is thought to break adhesion within Schlemm's canal, stretching the trabecular plates creating microperforations within the inner wall of the trabecular meshwork, thus allowing flow into Schlemm's canal, and separating herniations of the inner wall of the trabecular meshwork into the outer wall collector channels (see, e.g., Khaimi, M. A., "Canaloplasty: A Minimally Invasive and Maximally Effective Glaucoma Treatment", J. Ophthalmol., 2015, 2015:485065).

With the utilization of the Indigo Carmine containing ophthalmic compositions disclosed herein, it is possible to identify episcleral/aqueous veins and the deep scleral plexus, thereby allowing for the first time, injection of ophthalmic viscoelastic devices and/or drugs into this distal part of the aqueous drainage system. In certain embodiments, following instillation with an ophthalmic composition containing Indigo Carmine, and with the use of fine needles and cannulas (e.g., 35 gauge needle and 41 gauge cannula), the injection of fluid and ophthalmic viscoelastic devices, in a retrograde fashion, into this system can be accomplished by cannulating the larger aqueous/episcleral veins and slowly injecting in a retrograde fashion (see FIG. 5). This represents a new procedure, herein called Ab Externo Canaloplasty (sometimes referred to herein as ABeC). The Ab Externo Canaloplasty procedure is less invasive than ABiC, since no instruments need to be inserted into the eye—the only intraocular component of the procedure is injection of the ophthalmic composition containing Indigo Carmine via a very small gauge needle into the anterior chamber of the eye. In the ABiC procedure, the presumption is that "stretching" of angle structures is the reason for efficacy, a mechanical hypothesis. However, it may be that the hyaluronan component of the ophthalmic viscosurgical device (OVD) utilized during the ABiC procedure acts to induce VEGF-C (see, e.g., Jung, Y. J., et al., "Hyaluronan-induced VEGF-C promotes fibrosis-induced lymphangiogenesis via Toll-like receptor 4-dependent signal pathway", Biochem. Biophys. Res. Commun., 2015, 466: 339-45). This would allow Ab externo injection of concentrated hyaluronan rather than more viscous and difficult to inject substances. Injection of such solutions could be traced by using dyed solutions (more concentrated than initially used to trace the outflow pathways) to judge how much of the angle has been treated. Other potential drug treatments include injection of VEGF-C (see, e.g., Aspelund, A. et al., "The Schlemm's canal is a VEGF-C/VEGFR-3-responsive lymphatic-like vessel", J. Clin. Invest., 2014, 124:3975-86) or PROX1 (see, e.g., Park, D. Y., et al., "Lymphatic regulator PROX1 determines Schlemm's canal integrity and identity", J. Clin. Invest., 2014, 124:3960-74) inducers or appropriate regulating agents.

It has been shown that there are approximately 13 collector channels in the human eye (see, e.g., Cha, E. D., et al., "Variations in active outflow along the trabecular outflow pathway", Exp. Eye Res., 2016, 146:354-60). Accordingly, with the use of the Ab Externo Canaloplasty procedure, it would now be possible to identify each of them intraoperatively and to inject each in a retrograde fashion, thus treating the entire circumference of the drainage angle. Moreover, in the event obstructions exist, as per ABiC, then the Ab Externo Canaloplasty procedure could break them down "segmentally".

Figure 6:
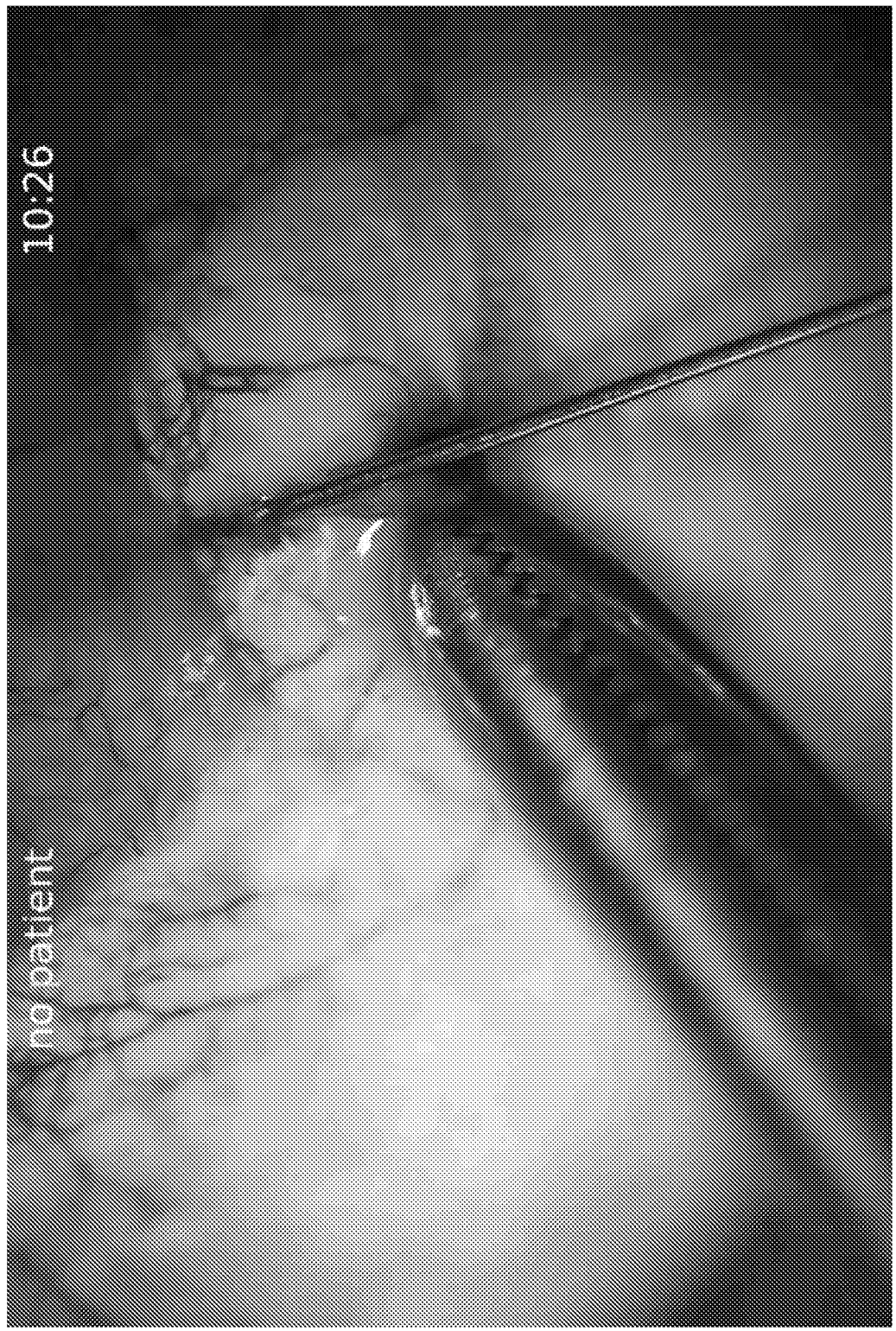
FIG. 6 is an operating microscope view of a human eye bank eye wherein, following identification of episcleral veins by injection of Indigo Carmine into the anterior chamber, it is possible to cannulate and inject the larger of these veins using either a small gauge needle or a retinal cannula (41 gauge).

The ophthalmic compositions containing Indigo Carmine also stain the anterior capsule of the crystalline lens, thereby allowing for easier visualization during cataract surgery (see FIG. 6). Importantly, since cataract surgery and glaucoma stent insertion are now frequently performed during the same operation, an ophthalmic composition containing both Indigo Carmine and Trypan Blue would facilitate both surgeries.

In certain embodiments, when Indigo Carmine is combined with other dyes, such as Trypan Blue, the concentration of both dyes can be reduced, thereby limiting any potential toxicity. For example, in certain embodiments, Trypan Blue is usually utilized in concentrations of 0.1-0.06 wt. %, and staining can occur with doses as low as 0.0125 wt. % (see, e.g., Yetik, H., et al., "Determining the lowest trypan blue concentration that satisfactorily stains the anterior capsule", J. Cataract Refract. Surg., 2002, 28:988-91). When combined with Indigo Carmine, the dosage of Trypan Blue can be further reduced to as little as 0.001 wt. %. For staining the cornea, the angle or other membranes in or on the eye (such as lens capsule or retinal membranes or corneal endothelial/Descemet's membrane preparations as used in endothelial keratoplasty, a form of lamellar corneal transplantation), the dosage of Indigo Carmine can also be reduced. In this way, the risk of toxicity from either dye can be minimized.

Figure 7:
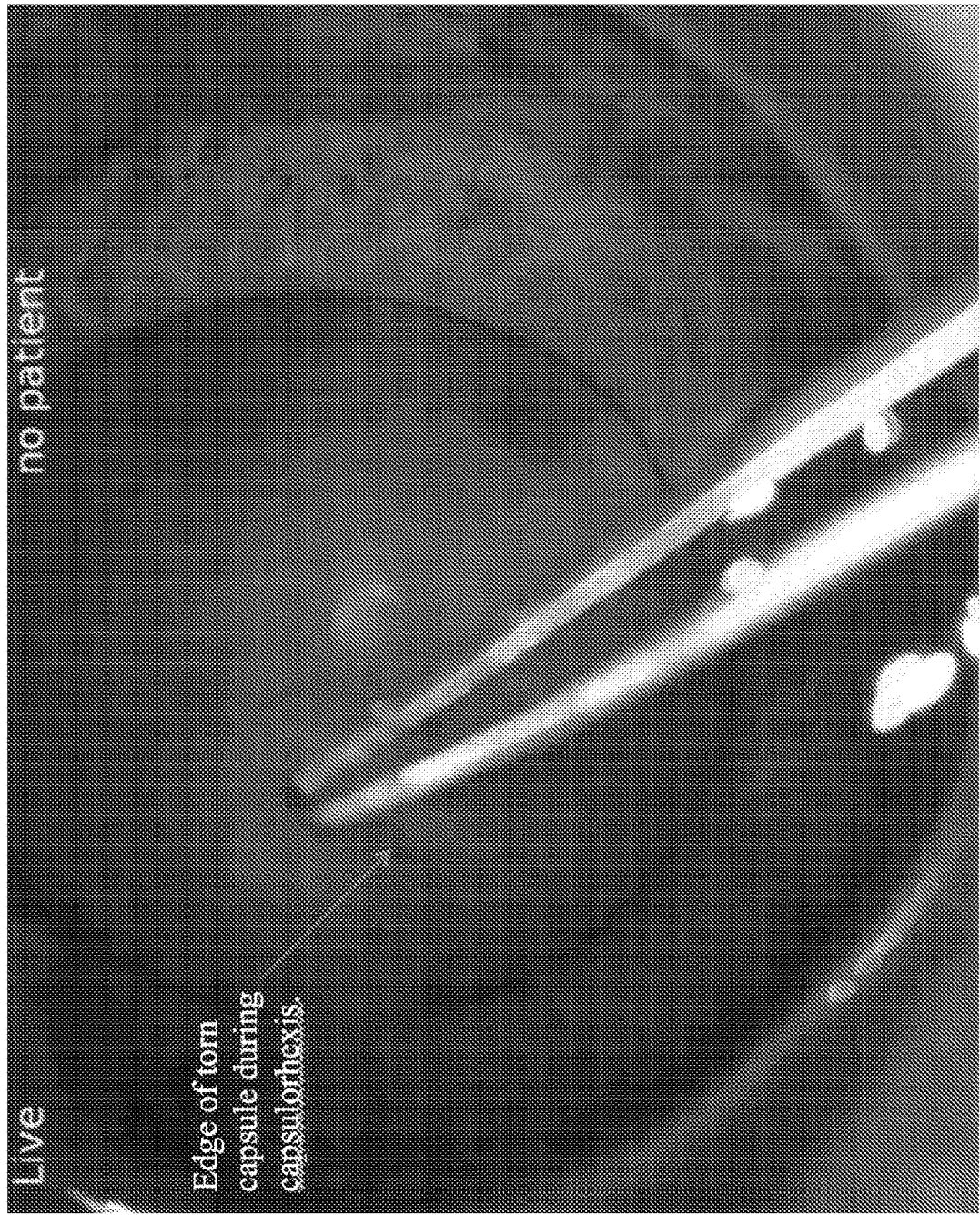
FIG. 7 is an operating microscope view of a human eye bank eye with Indigo Carmine injected into the anterior chamber via a small corneal incision during a capsulorhexis procedure. The anterior capsule of the lens is lightly stained with Indigo Carmine, enhancing its visibility.

In certain embodiments, the dye delineates eye surface dysplasia and malignancy (ocular surface squamous neoplasia) as has been found in the gut (see, e.g., Oyama, T., "Diagnostic strategies of superficial Barrett's esophageal cancer for endoscopic submucosal dissection", Dig. Endosc., 2013, 25 Suppl 1:7-12) (see FIG. 7)

In certain embodiments, the dye dissolves in the tear film and can be used for assessing tear film stability (in diseases such as dry eye syndrome) and epithelial loss of the cornea (punctate epithelial erosions) for which dyes such as fluorescein or lissamine green are currently used.

Similarly, in certain embodiments, when the endothelial (posterior layer) of the cornea fails, this layer can be replaced from donor material, introduced into the eye through a small incision in the procedure of endothelial keraroplasty. The disc of tissue to be transplanted is transparent and difficult to see once inserted into the eye. For this reason it is typically stained with a dye, Trypan Blue. However, a combined dye method, utilizing an ophthalmic composition comprising Indigo Carmine and Trypan Blue may be safer and provide better visualization than just by using Trypan Blue alone. Since endothelial keraroplasty can be carried out following cataract surgery, utilizing an ophthalmic composition comprising Indigo Carmine and Trypan Blue, which facilitates both surgeries, would be advantageous.

Figure 8:
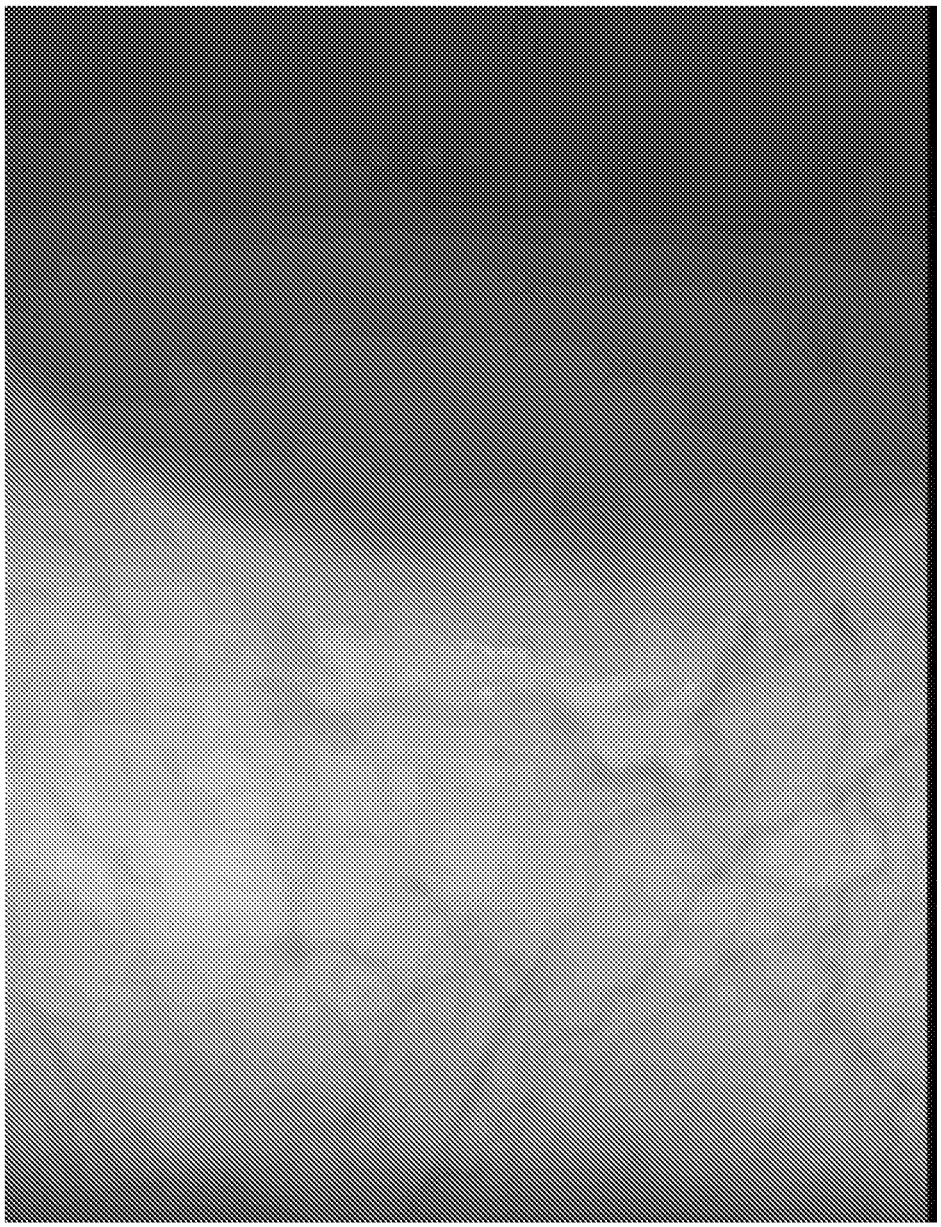
FIG. 8 is a slit lamp view of a human eye wherein an ocular surface squamous neoplastic lesion is delineated after topical application of Indigo Carmine. A blue outline is seen around the perimeter of the white ocular surface squamous neoplastic lesion.
Figure 9B:
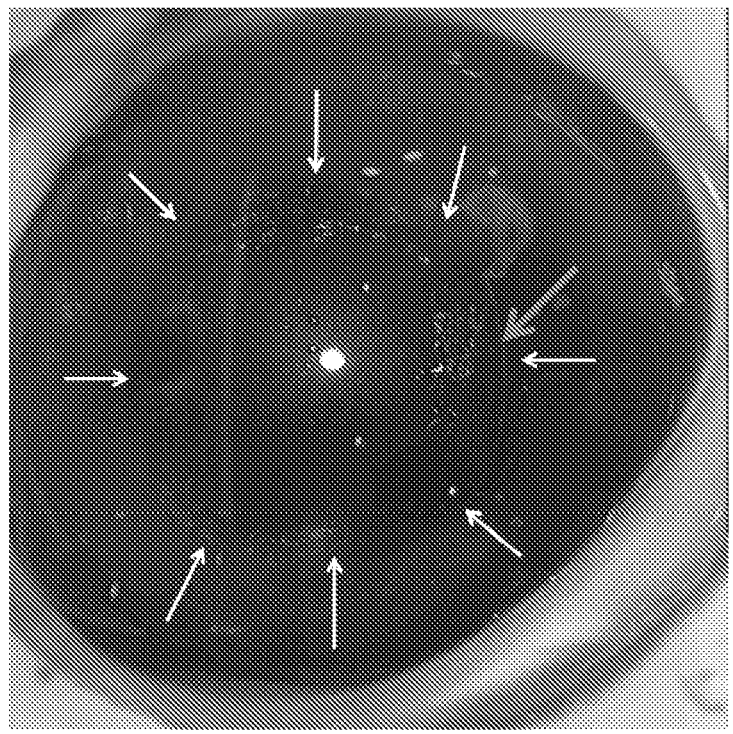
FIG. 9B is an operating microscope view of a porcine eye upon which a Small Incision Lenticule Extraction procedure (SMILE) has been carried out. Indigo Carmine has been injected into the lenticular plain. The white arrows indicate the complete circular edge of the lenticule. The red arrow shows the small incision into the lenticular plain through which the lenticule is removed.
Figure 9A:
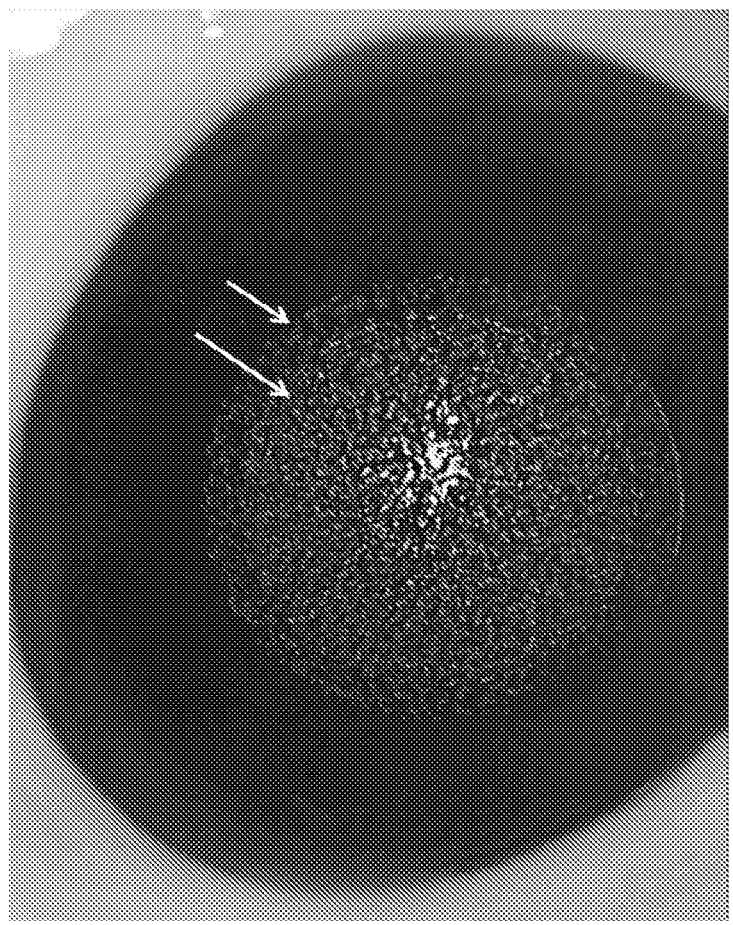
FIG. 9A is an operating microscope view of a porcine eye upon which a Small Incision Lenticule Extraction procedure (SMILE) has been carried out. From this view, circular horizontal plains have been cut in the corneal stroma, a superficial smaller diameter cut and a deeper cut of larger diameter. The cuts join in the corneal periphery, thereby creating a lenticule. The arrows show the edge of these cuts.

Minimally invasive corneal procedures for correcting refractive error (see, e.g., Titiyal, J. S., et al., "Learning Curve of Small Incision Lenticule Extraction: Challenges and Complications", Cornea, 2017, 36:1377-1382) have also been developed in recent years. For example, in Small Incision Lenticule Extraction (SIMILE), a lenticule of corneal stroma is created within the stroma using a laser and then removed through a small incision. Occasionally, the cuts that create the lenticule are discontinuous, making lenticule extraction difficult. This can result in damage to the corneal stroma in attempts to remove the lenticule, inability to remove the lenticule or incomplete removal of the lenticule, resulting in an irregular cornea, consequent astigmatism and poor vision. Since the cornea is transparent, identifying the lenticule after laser incisions have been made is problematic. By injecting an ophthalmic composition comprising Indigo Carmine into the cornea, for example, along the laser incision planes, it is possible to identify and determine the extent of these incisions, particularly the rounded edge of the lenticule (see FIG. 8), thereby identifying areas of incision discontinuity. These areas can then be manually separated so that either an intact lenticule can be removed or a missing piece of lenticule can be identified and removed separately. The relatively reduced protein binding of Indigo Carmine (compared to other ophthalmic dyes), and that it generally does not diffuse through tissues, makes it ideal for use during SMILE procedures.

EXAMPLES

The following ophthalmic compositions (dye solutions) used were aqueous solutions containing Indigo Carmine+/−Trypan Blue, wherein the concentration of the Trypan Blue present is 0.1 wt. % or less.

Dye Instillation Procedure:

After an incision is made into the anterior chamber of the eye, a small amount of aqueous humor is expressed and the dye solution is instilled by injection into the anterior chamber. The dye solution is typically left in place for 30 seconds, during which time it stains the anterior capsule of the lens. Excess dye solution is then expelled, usually using a viscoelastic device or flushed out with a balanced salt solution.

Ocular Surgery:

The dye instillation procedure detailed above is suitable for ocular surgeries, such as cataract surgery, glaucoma surgery, combination cataract/glaucoma surgery, minimally invasive glaucoma surgery (MIGS), retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, ocular surface diagnostic technique, and combinations thereof.

For cataract surgery, this dye instillation procedure enables enhanced visualization of the lens capsule when it is incised.

For glaucoma surgery, such as minimally invasive glaucoma surgery (MIGS), after instillation of the dye solution, stents may be placed in the now stained eye:

i) if a stent is to be placed in canal of Schlemm, the site of egress of the dye solution in the episcleral veins will be noted and stents (like iStent) are to be placed adjacent to these areas of maximal outflow.

ii) if the stent is to be placed in the suprachoroidal space (CyPass), the dye solution (containing Indigo Carmine+/−Trypan Blue) stains both canal of Schelmm and trabecular meshwork, thereby enabling precise identification of structures in the angle of the eye, so the stent can be more precisely and accurately placed.

After insertion of the stent(s), more dye solution can be flushed through the anterior chamber, via the stents and out of the anterior chamber, to confirm the potency of the placed stent(s).

For Ab Externo Canaloplasty (ABeC), after instillation of the dye solution, the stained collector channel(s) and episcleral vein(s) are identified, so one or more of the collector channels and episcleral veins can be cannulated. Some flushing with balanced salt will then be carried out to clear some of the dye solution. Next, a dye solution containing Indigo Carmine+/−Trypan Blue, either in the usual balanced salt solution or in a viscolesatic device, will be injected retrogradely to fill the canal of Schlemm. In some instances, the concentration of the Indigo Carmine in the dye injected into the canal of Schlemm may be more concentrated than used initially so as to better visualize the canal, and in some instances, multiple injections will be required into each of the major episcleral veins.

For corneal procedures, such as Descemet's Membrane Endothelial Keratoplasty (DMEK), the tissue to be transplanted is prepared and it is placed in the dye solution long enough for staining to occur, though the time is kept to a minimum to reduce any possibility of toxicity.

Example 1

Dye solutions containing 0.004 wt. %, 0.04 wt. %, and 0.4 wt. % of Indigo Carmine (prepared by serial dilutions of a 0.4 wt. % Indigo Carmine solution provided by Micro-Tech (Nanjing) Co.) were instilled by injection into the anterior chamber of seven eye bank eyes following the dye solution instillation procedure detailed above.

Figure 2:
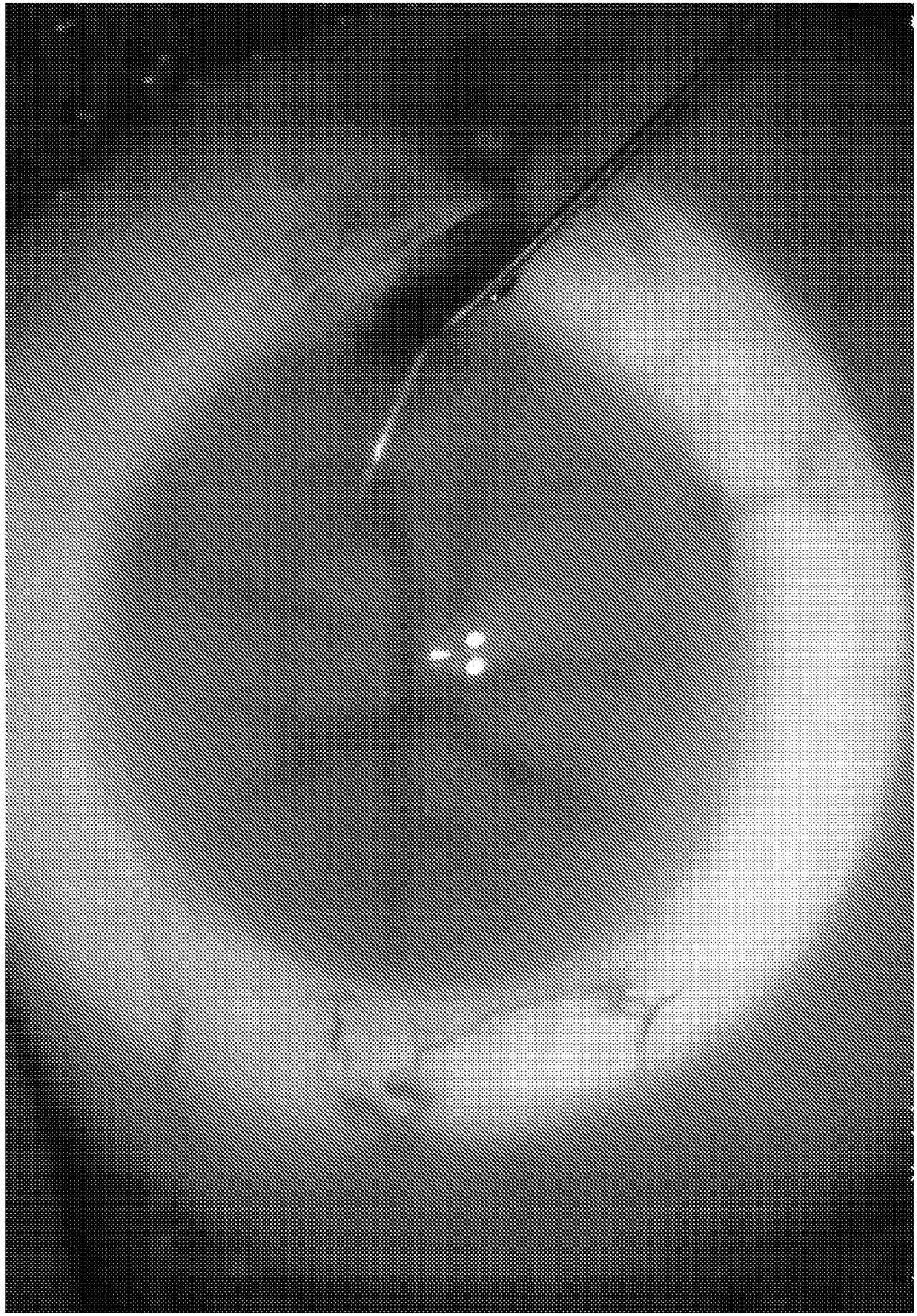
FIG. 2 is an operating microscope view of a human eye bank eye with Indigo Carmine injected into the anterior chamber via a small corneal incision, with some of the dye exiting the eye through the aqueous veins. The segmental nature of the episcleral vein distribution is observed in this eye from a 74 year older donor.
Figure 3:
FIG. 3 is an operating microscope view of a human eye bank eye with Indigo Carmine injected into the anterior chamber via a small corneal incision when the conjunctiva is reflected, deeper vessels are seen, evidence of the deep scleral plexus.

After a short delay from the start of the infusion/injection, the Indigo Carmine dye appeared in the fine vessels in the conjunctiva adjacent to the limbus, the aqueous veins and the conjunctival venous system. The Indigo Carmine dye was easily visible to the naked eye of the surgeon as it appeared on the surface of the dye instilled eye, and detailed branching of the vessels delineated were visible using a standard operating microscope routinely used in glaucoma surgery (see FIG. 2). Special imaging techniques were not required. The Indigo Carmine dye was also observed in the deep scleral plexus, once the conjunctiva was reflected away (see FIG. 3). The Indigo Carmine dye, at each concentration noted above, was visible to the naked eye of the surgeon as it appeared in the collector channels on the surface of the eye after it had passed through the drainage system.

The observed staining achieved by the Indigo Carmine dye solution is in contrast with that observed with other ophthalmic dyes, such as Trypan Blue (e.g., VISION-BLUE®, containing 0.06 wt. % Trypan Blue), Brilliant Blue, Patent Blue, and Indocyanine Green. Specifically, unlike with the Indigo Carmine dye solution, after injection of the other ophthalmic dyes (Trypan Blue, Brilliant Blue, Patent Blue, or Indocyanine Green), the dye appears to remain within the eye. This is likely due to the fact that these other ophthalmic dyes are bound within the angle to entities such as glycosaminoglycans (GAGS), proteins or to other molecules or structures within the drainage angle. Similarly, an injection with the ophthalmic dye Fluorescein tends to diffuse through the tissues and is not very useful in specifically detecting the drainage pathways.

Figure 4:
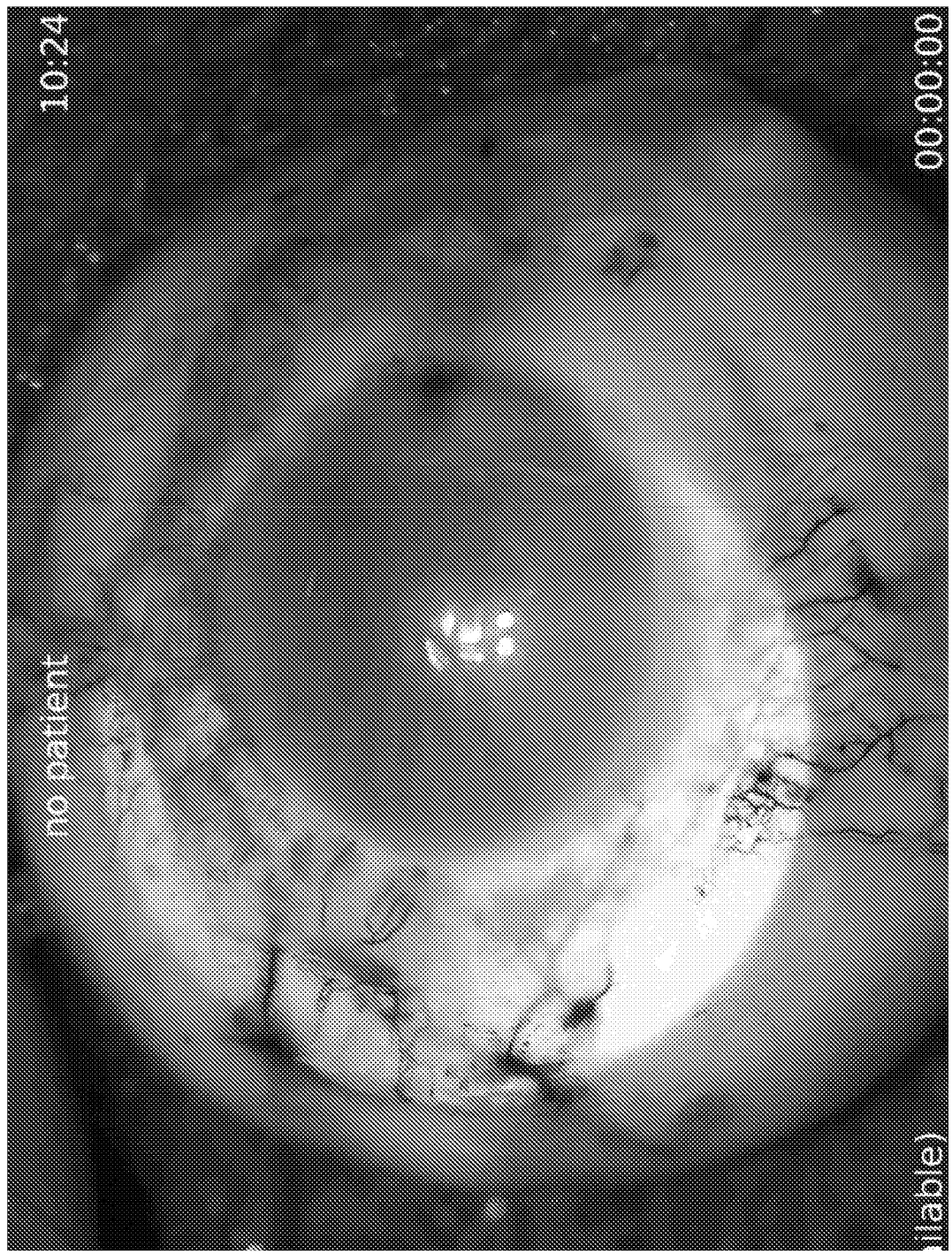
FIG. 4 is an operating microscope view of a human eye bank eye with Indigo Carmine injected into the anterior chamber via a small corneal incision, with some of the dye exiting the eye through the aqueous veins. The human eye bank eye is from a 36 year old donor, in which a more extensive distribution of episcleral veins than in the older donor eye (FIG. 2), can be seen.

As predicted from recent studies on the collector channels (see, e.g., Hann, C. R., et al., "Anatomic changes in Schlemm's canal and collector channels in normal and primary open-angle glaucoma eyes using low and high perfusion pressures", Invest. Ophthalmol. Vis. Sci., 2014 Aug. 19, 55(9):5834-41; Wirbelauer, C., et al., "Role of Intraoperative Indirect Channelography in Glaucoma Stent Implantation", Klin. Monbl. Augenheilkd., 2017, 234:1378-1386; Huang, A. S., et al., "Aqueous Angiography: Aqueous Humor Outflow Imaging in Live Human Subjects", Ophthalmology, 2017, 124:1249-1251; and Saraswathy, S., et al., "Aqueous Angiography: Real-Time and Physiologic Aqueous Humor Outflow Imaging", PLoS One, 2016 Jan. 25, 11(1):e0147176), the distribution of this drainage pattern is not uniform, which may be an age related phenomenon (see FIG. 4, and see FIG. 2).

Figure 5:
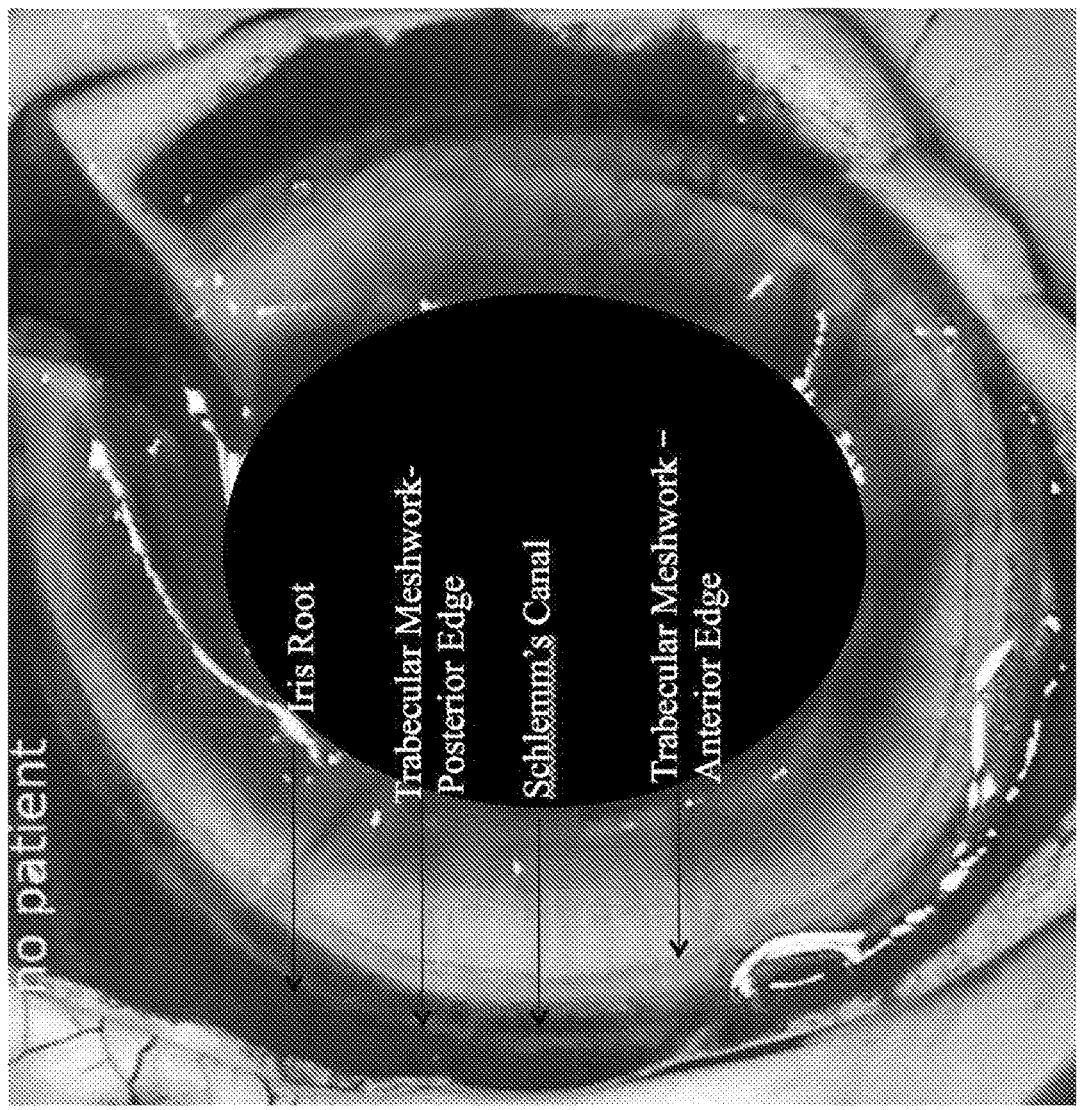
FIG. 5 is an operating microscope view of a surgically excised anterior segment of an eye bank eye after the anterior chamber has been perfused with an Indigo Carmine solution. The central cornea has been trephined (black oval area) and the specimen viewed from behind (as if one is standing on the retina and looking forward). The dark circular ring represents heavy staining of Schlemm's canal. The more lightly stained rings anterior and posterior to Schlemm's canal represent the anterior and posterior aspects of the trabecular meshwork. The iris root is seen beyond the posterior trabecular meshwork attachment.

As can be observed in FIG. 5, the Indigo Carmine dye stains the trabecular meshwork lightly and enters the canal of Schlemm, which stains heavily, allowing for easier identification of these structures. The staining of these structures is critical for the insertion of modern glaucoma stents, as these landmarks can be difficult to see intraoperatively. FIG. 5 shows how the trabecular meshwork and the canal of Schlemm are stained, bringing them into stark contrast against the surrounding tissue. This allows accurate placement of stents either in the canal of Schlemm or into the suprachoroidal space—since this technique require identification of the scleral spur (FIG. 1A). The posterior aspect of the trabecular meshwork attaches to the scleral spur, which can now be accurately visualized by the Indigo Carmine dye (FIG. 5). Suprachoroidal stents are inserted just posterior to the scleral spur, and into the suprachoridal space.

The trabecular meshwork is particularly well seen with a dye solution containing a combination of Indigo Carmine and Trypan Blue, since the Trypan Blue particularly enhances trabecular meshwork staining.

Utilization of the Indigo Carmine dye for ophthalmic staining facilitates the determination of both the location and the type of stent to be used. In situations where there is little outflow into the collector channel/aqueous/episcleral vein system, then a suprachoroidal stent would be used, since there is "nowhere to go" via the conventional drainage pathway in the angle of the eye. In situations where collector channels are identified, then a stent placed in the canal of Schlemm may be preferable and these stents would be placed adjacent to the sectors with good collector channel drainage. In certain situations, several stents could be placed in this way to take advantage of good "downstream" drainage.

Exemplary Embodiments

In an embodiment, an ophthalmic composition, comprising Indigo Carmine.

In an embodiment, an ophthalmic composition, comprising Indigo Carmine and Trypan Blue.

In an embodiment, a method for ocular surgery in a patient in need thereof, comprising instilling an ophthalmic composition comprising Indigo Carmine into the patient's eye.

In an embodiment, a method for ocular surgery in a patient in need thereof, comprising instilling an ophthalmic composition comprising Indigo Carmine and Trypan Blue into the patient's eye.

In an embodiment, a method for ocular surgery in a patient in need thereof, comprising: instilling an ophthalmic composition comprising Indigo Carmine and an ophthalmic composition comprising Trypan Blue into the patient's eye.

In an embodiment, a method for identifying an intraocular structure(s) or membrane(s) within an eye of a patient in need thereof, comprising instilling an ophthalmic composition comprising Indigo Carmine into the patient's eye.

In an embodiment, a method for identifying an intraocular structure(s) or membrane(s) within an eye of a patient in need thereof, comprising instilling an ophthalmic composition comprising Indigo Carmine and Trypan Blue into the patient's eye.

In an embodiment, a method for identifying an intraocular structure(s) or membrane(s) within an eye of a patient in need thereof, comprising: instilling an ophthalmic composition comprising Indigo Carmine and an ophthalmic composition comprising Trypan Blue into the patient's eye.

In an embodiment, a method for introducing an ophthalmic device into an eye of a patient in need thereof, comprising:
  i) instilling an ophthalmic composition comprising Indigo Carmine into the patient's eye; and
  ii) introducing the ophthalmic device into the instilled eye.

In an embodiment, a method for introducing an ophthalmic device into an eye of a patient in need thereof, comprising:
  i) instilling an ophthalmic composition comprising Indigo Carmine and Trypan Blue into the patient's eye; and
  ii) introducing the ophthalmic device into the instilled eye.

In an embodiment, a method for introducing an ophthalmic device into an eye of a patient in need thereof, comprising:
  i) instilling an ophthalmic composition comprising Indigo Carmine and an ophthalmic composition comprising Trypan Blue into the patient's eye; and
  ii) introducing the ophthalmic device into the instilled eye.

In an embodiment, a method for identification of canal of Schlemm within an eye of a patient in need thereof, comprising instilling an ophthalmic composition comprising Indigo Carmine the patient's eye.

In an embodiment, a method for identification of canal of Schlemm within an eye of a patient in need thereof, comprising instilling an ophthalmic composition comprising Indigo Carmine and Trypan Blue the patient's eye.

In an embodiment, a method for identification of canal of Schlemm within an eye of a patient in need thereof, comprising instilling an ophthalmic composition comprising Indigo Carmine and an ophthalmic composition comprising Trypan Blue into the patient's eye.

In an embodiment, a method of cataract extraction and treatment of glaucoma in an eye of a patient in need thereof, comprising:
  i) instilling an ophthalmic composition comprising Trypan Blue into the patient's eye;
  ii) surgically extracting the cataract of the Trypan Blue instilled eye;
  iii) instilling an ophthalmic composition comprising Indigo Carmine into the cataract extracted eye; and
  iv) surgically treating the glaucoma of the Indigo Carmine instilled eye.

In an embodiment, a method of cataract extraction and treatment of glaucoma in an eye of a patient in need thereof, comprising:
  i) instilling an ophthalmic composition comprising Indigo Carmine into the patient's eye;
  ii) surgically extracting the cataract of the instilled eye; and
  iii) surgically treating the glaucoma of the cataract extracted eye.

In an embodiment, a method of cataract extraction and treatment of glaucoma in an eye of a patient in need thereof, comprising:
  i) instilling an ophthalmic composition comprising Indigo Carmine and Trypan Blue into the patient's eye;
  ii) surgically extracting the cataract of the instilled eye; and
  iii) surgically treating the glaucoma of the cataract extracted eye.

In an embodiment, a method of cataract extraction and treatment of glaucoma in an eye of a patient in need thereof, comprising:
  i) instilling an ophthalmic composition comprising Indigo Carmine and an ophthalmic composition comprising Trypan Blue into the patient's eye;
  ii) surgically extracting the cataract of the instilled eye; and
  iii) surgically treating the glaucoma of the cataract extracted eye.

In certain embodiments, one or more than one (including for instance all) of the following further embodiments may comprise each of the other embodiments or parts thereof.

In a further embodiment, the ophthalmic composition, or the method, of any one of the above embodiments and any one or more of the further embodiments herein, wherein the ophthalmic composition is an aqueous composition.

In a further embodiment, the ophthalmic composition, or the method, of any one of the above embodiments and any one or more of the further embodiments herein, wherein the Indigo Carmine is present in an amount in the range of between approximately 0.001-0.4 wt. %, relative to the ophthalmic composition.

In a further embodiment, the ophthalmic composition, or the method, of any one of the above embodiments and any one or more of the further embodiments herein, wherein the Indigo Carmine is present in an amount in the range of between approximately 0.001-0.3 wt. %, between approximately 0.001-0.2 wt. %, between approximately 0.001-0.1 wt. %, between approximately 0.001-0.05 wt. %, between approximately 0.001-0.01 wt. %, between approximately 0.005-0.4 wt. %, between approximately 0.005-0.3 wt. %, between approximately 0.005-0.2 wt. %, between approximately 0.005-0.1 wt. %, between approximately 0.005-0.05 wt. %, between approximately 0.005-0.01 wt. %, between approximately 0.004-0.4 wt. %, between approximately 0.004-0.04 wt. %, between approximately 0.01-0.35 wt. %, between approximately 0.01-0.3 wt. %, between approximately 0.01-0.25 wt. %, between approximately 0.01-0.2 wt. %, between approximately 0.01-0.15 wt. %, between approximately 0.01-0.1 wt. %, between approximately 0.04-0.4 wt. %, between approximately 0.05-0.4 wt. %, between approximately 0.1-0.4 wt. %, between approximately 0.15-0.4 wt. %, between approximately 0.2-0.4 wt. %, between approximately 0.25-0.4 wt. %, between approximately 0.3-0.4 wt. %, between approximately 0.35-0.4 wt. %, between approximately 0.1-0.3 wt. %, between approximately 0.1-0.2 wt. %, between approximately 0.01-0.05 wt. %, or between approximately 0.05-0.1 wt. %, relative to the ophthalmic composition.

In a further embodiment, the ophthalmic composition, or the method, of any one of the above embodiments and any one or more of the further embodiments herein, wherein the Indigo Carmine is present in an amount of approximately 0.001 wt. %, approximately 0.002 wt. %, approximately 0.003 wt. %, approximately 0.004 wt. %, approximately 0.005 wt. %, approximately 0.006 wt. %, approximately 0.007 wt. %, approximately 0.008 wt. %, approximately 0.009 wt. %, approximately 0.01 wt. %, approximately 0.02 wt. %, approximately 0.03 wt. %, approximately 0.04 wt. %, approximately 0.05 wt. %, approximately 0.06 wt. %, approximately 0.07 wt. %, approximately 0.08 wt. %, approximately 0.09 wt. %, approximately 0.1 wt. %, approximately 0.2 wt. %, approximately 0.3 wt. %, or approximately 0.4 wt. %, relative to the ophthalmic composition.

In a further embodiment, the ophthalmic composition, or the method, of any one of the above embodiments and any one or more of the further embodiments herein, wherein the Indigo Carmine is present in an amount of at least 0.001 wt. %, at least 0.002 wt. %, at least 0.003 wt. %, at least 0.004 wt. %, at least 0.005 wt. %, at least 0.006 wt. %, at least 0.007 wt. %, at least 0.008 wt. %, at least 0.009 wt. %, at least 0.01 wt. %, at least 0.02 wt. %, at least 0.03 wt. %, at least 0.04 wt. %, at least 0.05 wt. %, at least 0.06 wt. %, at least 0.07 wt. %, at least 0.08 wt. %, at least 0.09 wt. %, at least 0.1 wt. %, at least 0.15 wt. %, at least 0.2 wt. %, at least 0.25 wt. %, at least 0.3 wt. %, or at least 0.35 wt. %, relative to the ophthalmic composition.

In a further embodiment, the ophthalmic composition, or the method, of any one of the above embodiments and any one or more of the further embodiments herein, wherein the ophthalmic composition further comprises Trypan Blue.

In a further embodiment, the ophthalmic composition, or the method, of any one of the above embodiments and any one or more of the further embodiments herein, wherein the Trypan Blue is present in an amount in the range of between approximately 0.001-0.1 wt. %, relative to the ophthalmic composition.

In a further embodiment, the ophthalmic composition, or the method, of any one of the above embodiments and any one or more of the further embodiments herein, wherein the Trypan Blue is present in an amount less than 0.1 wt. %, relative to the ophthalmic composition.

In a further embodiment, the ophthalmic composition, or the method, of any one of the above embodiments and any one or more of the further embodiments herein, wherein the Trypan Blue is present in an amount less than 0.05 wt. %, less than 0.04 wt. %, less than 0.03 wt. %, less than 0.02 wt. %, or less than 0.01 wt. %, relative to the ophthalmic composition.

In a further embodiment, the ophthalmic composition, or the method, of any one of the above embodiments and any one or more of the further embodiments herein, wherein the Trypan Blue is present in an amount in the range of between approximately 0.001-0.05 wt. %, between approximately 0.001-0.045 wt. %, between approximately 0.001-0.04 wt. %, between approximately 0.001-0.035 wt. %, between approximately 0.001-0.03 wt. %, between approximately 0.001-0.025 wt. %, between approximately 0.001-0.02 wt. %, between approximately 0.001-0.015 wt. %, between approximately 0.001-0.01 wt. %, between approximately 0.005-0.1 wt. %, between approximately 0.005-0.05 wt. %, between approximately 0.005-0.045 wt. %, between approximately 0.005-0.04 wt. %, between approximately 0.005-0.035 wt. %, between approximately 0.005-0.03 wt. %, between approximately 0.005-0.025 wt. %, between approximately 0.005-0.02 wt. %, between approximately 0.005-0.015 wt. %, between approximately 0.005-0.01 wt. %, between approximately 0.01-0.1 wt. %, between approximately 0.01-0.05 wt. %, between approximately 0.01-0.045 wt. %, between approximately 0.01-0.04 wt. %, between approximately 0.01-0.035 wt. %, between approximately 0.01-0.03 wt. %, between approximately 0.01-0.025 wt. %, between approximately 0.01-0.02 wt. %, between approximately 0.01-0.015 wt. %, or between approximately 0.02-0.04 wt. %, relative to the ophthalmic composition.

In a further embodiment, the ophthalmic composition, or the method, of any one of the above embodiments and any one or more of the further embodiments herein, wherein the Trypan Blue is present in an amount of approximately 0.001 wt. %, approximately 0.005 wt. %, approximately 0.01 wt. %, approximately 0.015 wt. %, approximately 0.02 wt. %, approximately 0.025 wt. %, approximately 0.03 wt. %, approximately 0.035 wt. %, approximately 0.04 wt. %, approximately 0.045 wt. %, approximately 0.05 wt. %, or approximately 0.1 wt. %, relative to the ophthalmic composition.

In a further embodiment, the ophthalmic composition, or the method, of any one of the above embodiments and any one or more of the further embodiments herein, wherein the ophthalmic composition comprises Indigo Carmine in an amount in the range of between approximately 0.001-0.4 wt. %, and the Trypan Blue in an amount in the range of between approximately 0.001-0.1 wt. %, relative to the ophthalmic composition, for example, comprises Indigo Carmine in an amount in the range of between approximately 0.005-0.3 wt. %, and Trypan Blue in an amount in the range of between approximately 0.005-0.05 wt. %, relative to the ophthalmic composition, such as comprises Indigo Carmine in an amount in the range of between approximately 0.005-0.3 wt. %, and Trypan Blue in an amount in the range of between approximately 0.005-0.045 wt. %, relative to the ophthalmic composition, comprises Indigo Carmine in an amount in the range of between approximately 0.005-0.3 wt. %, and Trypan Blue in an amount in the range of between approximately 0.005-0.04 wt. %, relative to the ophthalmic composition; or comprises Indigo Carmine in an amount of approximately 0.01 wt. %, and Trypan Blue in an amount of approximately 0.01 wt. %, relative to the ophthalmic composition.

In a further embodiment, the ophthalmic composition, or the method, of any one of the above embodiments and any one or more of the further embodiments herein, wherein the ophthalmic composition comprises 0.4 wt. % of Indigo Carmine and 0.06 wt. % Trypan Blue, relative to the ophthalmic composition.

In a further embodiment, the ophthalmic composition, or the method, of any one of the above embodiments and any one or more of the further embodiments herein, wherein an ophthalmic composition comprising Indigo Carmine (for example, Indigo Carmine in an amount in the range of between approximately 0.001-0.4 wt. %, such as 0.4 wt. % of Indigo Carmine, relative to the ophthalmic composition) is co-administered with an ophthalmic composition comprising Trypan Blue (for example, Trypan Blue in an amount in the range of between approximately 0.001-0.1 wt. %, such as 0.06 wt. % Trypan Blue, relative to the ophthalmic composition), wherein the co-administration of the ophthalmic composition comprising Trypan Blue is as at the same time, or sequentially before or after.

In a further embodiment, the ophthalmic composition, or the method, of any one of the above embodiments and any one or more of the further embodiments herein, wherein the ophthalmic composition further comprises Brilliant Blue.

In a further embodiment, the ophthalmic composition, or the method, of any one of the above embodiments and any one or more of the further embodiments herein, wherein the ophthalmic composition further comprises Patent Blue.

In a further embodiment, the ophthalmic composition, or the method, of any one of the above embodiments and any one or more of the further embodiments herein, wherein the ophthalmic composition further comprises Indocyanine Green.

In a further embodiment, the ophthalmic composition, or the method, of any one of the above embodiments and any one or more of the further embodiments herein, wherein the ophthalmic composition further comprises Fluorescein.

In a further embodiment, the ophthalmic composition, or the method, of any one of the above embodiments and any one or more of the further embodiments herein, wherein the ophthalmic composition is an injectable ophthalmic formulation.

In a further embodiment, the ophthalmic composition, or the method, of any one of the above embodiments and any one or more of the further embodiments herein, wherein the ophthalmic composition is a sterile aqueous solution.

In a further embodiment, the ophthalmic composition, or the method, of any one of the above embodiments and any one or more of the further embodiments herein, wherein the ophthalmic composition comprises or is an ophthalmic irrigation solution.

In a further embodiment, the ophthalmic composition, or the method, of any one of the above embodiments and any one or more of the further embodiments herein, wherein the ophthalmic irrigation solution may be a balanced salt solution (BSS), a Balanced Salt Solution Plus (BSS Plus®), an Alsever's salt solution, an Earle's balanced salt solution (EBSS), a Gey's balanced salt solution (GBSS), a Hanks' balanced salt solution (HMS), a Dulbecco's phosphate buffered saline (PBS), a Puck's balanced salt solution, a Ringer's balanced salt solution (RBSS), a Simm's balanced salt solution (SBSS), a TRIS-buffered saline (TBS), or a Tyrode's balanced salt solution solution (TBSS), or combinations thereof.

In a further embodiment, the ophthalmic composition, or the method, of any one of the above embodiments and any one or more of the further embodiments herein, wherein the ophthalmic composition comprises sugar compounds, such as glucose or dextrose.

In a further embodiment, the ophthalmic composition, or the method, of any one of the above embodiments and any one or more of the further embodiments herein, wherein the ophthalmic composition comprises anti-oxidant compounds, such as glutathione.

In a further embodiment, the ophthalmic composition, or the method, of any one of the above embodiments and any one or more of the further embodiments herein, wherein the ophthalmic composition is an isotonic, aqueous solution, such as an isotonic, sterile, aqueous solution, having a neutral pH, such as a between pH 6-8, between pH 6.5-7.5, between pH 7-7.6, between pH 7.3-7.6, or between pH 6.8-7.2, or about pH 7.

In a further embodiment, the ophthalmic composition, or the method, of any one of the above embodiments and any one or more of the further embodiments herein, wherein the ophthalmic composition comprises sodium, potassium, calcium, and/or magnesium cations.

In a further embodiment, the ophthalmic composition, or the method, of any one of the above embodiments and any one or more of the further embodiments herein, wherein the ophthalmic composition comprises phosphate ion, mono-hydrogen phosphate ion, di-hydrogen phosphate ion, citrate ion, bicarbonate, or chloride ion, or combinations thereof.

In a further embodiment, the ophthalmic composition, or the method, of any one of the above embodiments and any one or more of the further embodiments herein, wherein the ophthalmic composition comprises inorganic salts and/or organic salts.

In a further embodiment, the ophthalmic composition, or the method, of any one of the above embodiments and any one or more of the further embodiments herein, wherein the inorganic salts and/or organic salts comprises sodium chloride, potassium chloride, calcium chloride, magnesium chloride, sodium acetate, sodium phosphate, sodium mono-hydrogen phosphate (sodium mono-hydrogen orthophosphate), sodium di-hydrogen phosphate (sodium di-hydrogen orthophosphate), sodium bicarbonate, or sodium citrate, or combinations thereof.

In a further embodiment, the ophthalmic composition, or the method, of any one of the above embodiments and any one or more of the further embodiments herein, wherein the ophthalmic composition has an osmolality between 200-400 mosmol/kg, such as 250-350 mosmol/kg, 300-350 mosmol/kg, or 250-325 mosmol/kg, for example, 200 mosm/kg, 250 mosm/kg, 275 mosm/kg, 300 mosm/kg, or 325 mosm/kg, such as 300 mosm/kg.

In a further embodiment, the ophthalmic composition, or the method, of any one of the above embodiments and any one or more of the further embodiments herein, wherein the ophthalmic composition further comprises one or more additional ophthalmically acceptable excipients and additives.

In a further embodiment, the ophthalmic composition, or the method, of any one of the above embodiments and any one or more of the further embodiments herein, wherein the ophthalmic composition is used for application to an eye.

In a further embodiment, the ophthalmic composition, or the method, of any one of the above embodiments and any one or more of the further embodiments herein, wherein the application of the ophthalmic composition to the eye is via topical application to said eye.

In a further embodiment, the ophthalmic composition, or the method, of any one of the above embodiments and any one or more of the further embodiments herein, wherein the application of the ophthalmic composition to the eye is via injection into said eye.

In a further embodiment, the ophthalmic composition, or the method, of any one of the above embodiments and any one or more of the further embodiments herein, wherein the application of the ophthalmic composition to the eye is via injection into the anterior chamber of said eye.

In a further embodiment, the ophthalmic composition, or the method, of any one of the above embodiments and any one or more of the further embodiments herein, wherein the eye is a glaucomatous eye.

In a further embodiment, the ophthalmic composition, or the method, of any one of the above embodiments and any one or more of the further embodiments herein, wherein the eye has a cataract.

In a further embodiment, the ophthalmic composition, or the method, of any one of the above embodiments and any one or more of the further embodiments herein, wherein the method is a method for ocular surgery in a patient in need thereof, and wherein said method comprises instilling the ophthalmic composition of any one of the above embodiments and any one or more of the further embodiments.

In a further embodiment, the ophthalmic composition, or the method, of any one of the above embodiments and any one or more of the further embodiments herein, wherein the method includes an ocular surgery, or the ocular surgery is, selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, and ocular surface diagnostic technique.

In a further embodiment, the ophthalmic composition, or the method, of any one of the above embodiments and any one or more of the further embodiments herein, wherein the method, or the ocular surgery, includes a combination of two or more of the following ocular surgeries selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures such as removal of epiretinal membranes, and ocular surface diagnostic technique.

In a further embodiment, the ophthalmic composition, or the method, of any one of the above embodiments and any one or more of the further embodiments herein, wherein the ocular surgery is or includes glaucoma surgery.

In a further embodiment, the ophthalmic composition, or the method, of any one of the above embodiments and any one or more of the further embodiments herein, wherein the ocular surgery is or includes minimally invasive glaucoma surgery (MIGS).

In a further embodiment, the ophthalmic composition, or the method, of any one of the above embodiments and any one or more of the further embodiments herein, wherein the ocular surgery is or includes cataract surgery.

In a further embodiment, the ophthalmic composition, or the method, of any one of the above embodiments and any one or more of the further embodiments herein, wherein the ocular surgery is or includes retinal surgery.

In a further embodiment, the ophthalmic composition, or the method, of any one of the above embodiments and any one or more of the further embodiments herein, wherein the ocular surgery is or includes lens replacement surgery.

In a further embodiment, the ophthalmic composition, or the method, of any one of the above embodiments and any one or more of the further embodiments herein, wherein the ocular surgery is or includes surgery to treat ocular trauma.

In a further embodiment, the ophthalmic composition, or the method, of any one of the above embodiments and any one or more of the further embodiments herein, wherein the ocular surgery is or includes refractive lensectomy.

In a further embodiment, the ophthalmic composition, or the method, of any one of the above embodiments and any one or more of the further embodiments herein, wherein the ocular surgery is or includes corneal surgery.

In a further embodiment, the ophthalmic composition, or the method, of any one of the above embodiments and any one or more of the further embodiments herein, wherein the ocular surgery comprises extracting a cataract and treating glaucoma.

In a further embodiment, the ophthalmic composition, or the method, of any one of the above embodiments and any one or more of the further embodiments herein, wherein the ocular surgery is or includes endothelial keratoplasty.

In a further embodiment, the ophthalmic composition, or the method, of any one of the above embodiments and any one or more of the further embodiments herein, wherein the ocular surgery is or includes Descemet's Membrane Endothelial Keratoplasty (DMEK).

In a further embodiment, the ophthalmic composition, or the method, of any one of the above embodiments and any one or more of the further embodiments herein, wherein the ocular surgery is or includes capsulorhexis.

In a further embodiment, the ophthalmic composition, or the method, of any one of the above embodiments and any one or more of the further embodiments herein, wherein the ocular surgery is or includes lamellar corneal transplantation.

In a further embodiment, the ophthalmic composition, or the method, of any one of the above embodiments and any one or more of the further embodiments herein, wherein the ocular surgery is or includes a minimally invasive corneal procedure.

In a further embodiment, the ophthalmic composition, or the method, of any one of the above embodiments and any one or more of the further embodiments herein, wherein the ocular surgery is or includes a minimally invasive corneal procedure corrects refractive error.

In a further embodiment, the ophthalmic composition, or the method, of any one of the above embodiments and any one or more of the further embodiments herein, wherein the ocular surgery is or includes a corneal refractive procedure.

In a further embodiment, the ophthalmic composition, or the method, of any one of the above embodiments and any one or more of the further embodiments herein, wherein the ocular surgery is or includes a small incision lenticule extraction (SMILE).

In a further embodiment, the ophthalmic composition, or the method, of any one of the above embodiments and any one or more of the further embodiments herein, wherein the ocular surgery is or includes an Ab interno Canaloplasty (ABiC).

In a further embodiment, the ophthalmic composition, or the method, of any one of the above embodiments and any one or more of the further embodiments herein, wherein the ocular surgery is or includes an Ab externo Canaloplasty (ABeC).

In a further embodiment, the ophthalmic composition, or the method, of any one of the above embodiments and any one or more of the further embodiments herein, wherein the ocular surgery is or includes an ocular surface diagnostic technique.

In a further embodiment, the ophthalmic composition, or the method, of any one of the above embodiments and any one or more of the further embodiments herein, wherein the ocular surgery is a combination of glaucoma surgery and cataract surgery.

In a further embodiment, the ophthalmic composition, or the method, of any one of the above embodiments and any one or more of the further embodiments herein, wherein the ocular surgery is a combination of minimally invasive glaucoma surgery (MIGS) and cataract surgery.

In a further embodiment, the ophthalmic composition, or the method, of any one of the above embodiments and any one or more of the further embodiments herein, wherein the ocular surgery is a combination of minimally invasive glaucoma surgery (MIGS) and endothelial keratoplasty.

In a further embodiment, the ophthalmic composition, or the method, of any one of the above embodiments and any one or more of the further embodiments herein, wherein the ocular surgery is a combination of endothelial keratoplasty and cataract surgery.

In a further embodiment, the ophthalmic composition, or the method, of any one of the above embodiments and any one or more of the further embodiments herein, wherein the patient's eye is glaucomatous.

In a further embodiment, the ophthalmic composition, or the method, of any one of the above embodiments and any one or more of the further embodiments herein, wherein the patient's eye has a cataract.

In a further embodiment, the ophthalmic composition, or the method, of any one of the above embodiments and any one or more of the further embodiments herein, wherein the ophthalmic composition is instilled into the eye by injection.

In a further embodiment, the ophthalmic composition, or the method, of any one of the above embodiments and any one or more of the further embodiments herein, wherein the ophthalmic composition is instilled into the eye by injection into the anterior chamber of the eye.

In a further embodiment, the ophthalmic composition, or the method, of any one of the above embodiments and any one or more of the further embodiments herein, wherein the ophthalmic composition is instilled into the eye by a plurality of injections.

In a further embodiment, the ophthalmic composition, or the method, of any one of the above embodiments and any one or more of the further embodiments herein, wherein the ophthalmic composition is instilled into the eye by a plurality of injections into the anterior chamber of the eye.

In a further embodiment, the ophthalmic composition, or the method, of any one of the above embodiments and any one or more of the further embodiments herein, wherein the method identifies, marks, or stains an intraocular structure(s) or membrane(s) within the patient's eye in a visually identifiable manner.

In a further embodiment, the ophthalmic composition, or the method, of any one of the above embodiments and any one or more of the further embodiments herein, wherein the method identifies, marks, or stains an intraocular structure(s) or membrane(s) within the patient's eye in a visually identifiable manner easily visible by the naked eye of a surgeon.

In a further embodiment, the ophthalmic composition, or the method, of any one of the above embodiments and any one or more of the further embodiments herein, wherein the intraocular structure(s) or membrane(s) within the patient's eye is identified, marked, or stained, in a visually identifiable manner.

In a further embodiment, the ophthalmic composition, or the method, of any one of the above embodiments and any one or more of the further embodiments herein, wherein a plurality of intraocular structures or membranes within the eye are identified, marked, or stained, in a visually identifiable manner.

In a further embodiment, the ophthalmic composition, or the method, of any one of the above embodiments and any one or more of the further embodiments herein, wherein the method facilitates ready identification of the intraocular structure(s) or membrane(s) within the eye.

In a further embodiment, the ophthalmic composition, or the method, of any one of the above embodiments and any one or more of the further embodiments herein, wherein the method identifies, marks, or stains a portion of the intraocular structure(s) or membrane(s) within the patient's eye.

In a further embodiment, the ophthalmic composition, or the method, of any one of the above embodiments and any one or more of the further embodiments herein, wherein the method identifies, marks, or stains a plurality of the intraocular structures or membranes within the patient's eye.

In a further embodiment, the ophthalmic composition, or the method, of any one of the above embodiments and any one or more of the further embodiments herein, wherein the identified, marked, or stained intraocular structure(s) or membrane(s) within the patient's eye is selected from a group consisting of: a fine vessel, an aqueous vein, an episcleral vein, a collector channel, a collector channel/aqueous/episcleral vein system, an aqueous drainage system, a conjunctival venous system, a deep scleral plexus, a deep scleral plexus visually identifiable once a conjunctiva is reflected away, a trabecular meshwork, a canal of Schlemm, a suprachoroidal space, a scleral spur, anterior capsule of a crystalline lens, cornea, lens capsule, a retinal membrane, a corneal endothelial membrane, and Descemet's membrane.

In a further embodiment, the ophthalmic composition, or the method, of any one of the above embodiments and any one or more of the further embodiments herein, wherein the identified, marked, or stained intraocular structure(s) or membrane(s) within the patient's eye is a fine vessel.

In a further embodiment, the ophthalmic composition, or the method, of any one of the above embodiments and any one or more of the further embodiments herein, wherein the identified, marked, or stained intraocular structure(s) or membrane(s) within the patient's eye is a fine vessel is in the conjunctiva adjacent to the limbus.

In a further embodiment, the ophthalmic composition, or the method, of any one of the above embodiments and any one or more of the further embodiments herein, wherein the identified, marked, or stained intraocular structure(s) or membrane(s) within the patient's eye is an aqueous vein.

In a further embodiment, the ophthalmic composition, or the method, of any one of the above embodiments and any one or more of the further embodiments herein, wherein the identified, marked, or stained intraocular structure(s) or membrane(s) within the patient's eye is an episcleral vein.

In a further embodiment, the ophthalmic composition, or the method, of any one of the above embodiments and any one or more of the further embodiments herein, wherein the identified, marked, or stained intraocular structure(s) or membrane(s) within the patient's eye is a collector channel.

In a further embodiment, the ophthalmic composition, or the method, of any one of the above embodiments and any one or more of the further embodiments herein, wherein the identified, marked, or stained intraocular structure(s) or membrane(s) within the patient's eye is a collector channel/aqueous/episcleral vein system.

In a further embodiment, the ophthalmic composition, or the method, of any one of the above embodiments and any one or more of the further embodiments herein, wherein the identified, marked, or stained intraocular structure(s) or membrane(s) within the patient's eye is an aqueous drainage system of said eye.

In a further embodiment, the ophthalmic composition, or the method, of any one of the above embodiments and any one or more of the further embodiments herein, wherein the identified, marked, or stained intraocular structure(s) or membrane(s) within the patient's eye is conventional drainage system of said eye.

In a further embodiment, the ophthalmic composition, or the method, of any one of the above embodiments and any one or more of the further embodiments herein, wherein the identified, marked, or stained intraocular structure(s) or membrane(s) within the patient's eye is a conjunctival venous system.

In a further embodiment, the ophthalmic composition, or the method, of any one of the above embodiments and any one or more of the further embodiments herein, wherein the identified, marked, or stained intraocular structure(s) or membrane(s) within the patient's eye is a deep scleral plexus.

In a further embodiment, the ophthalmic composition, or the method, of any one of the above embodiments and any one or more of the further embodiments herein, wherein the identified, marked, or stained intraocular structure(s) or membrane(s) within the patient's eye is a deep scleral plexus visually identifiable once the conjunctiva is reflected away.

In a further embodiment, the ophthalmic composition, or the method, of any one of the above embodiments and any one or more of the further embodiments herein, wherein the identified, marked, or stained intraocular structure(s) or membrane(s) within the patient's eye is a trabecular meshwork.

In a further embodiment, the ophthalmic composition, or the method, of any one of the above embodiments and any one or more of the further embodiments herein, wherein the identified, marked, or stained intraocular structure(s) or membrane(s) within the patient's eye is a posterior aspect of a trabecular meshwork.

In a further embodiment, the ophthalmic composition, or the method, of any one of the above embodiments and any one or more of the further embodiments herein, wherein the identified, marked, or stained intraocular structure(s) or membrane(s) within the patient's eye is a canal of Schlemm.

In a further embodiment, the ophthalmic composition, or the method, of any one of the above embodiments and any one or more of the further embodiments herein, wherein the identified, marked, or stained intraocular structure(s) or membrane(s) within the patient's eye is a suprachoroidal space.

In a further embodiment, the ophthalmic composition, or the method, of any one of the above embodiments and any one or more of the further embodiments herein, wherein the identified, marked, or stained intraocular structure(s) or membrane(s) within the patient's eye is a scleral spur.

In a further embodiment, the ophthalmic composition, or the method, of any one of the above embodiments and any one or more of the further embodiments herein, wherein the identified, marked, or stained intraocular structure(s) or membrane(s) within the patient's eye is the anterior capsule of a crystalline lens.

In a further embodiment, the ophthalmic composition, or the method, of any one of the above embodiments and any one or more of the further embodiments herein, wherein the identified, marked, or stained intraocular structure(s) or membrane(s) within the patient's eye is a cornea.

In a further embodiment, the ophthalmic composition, or the method, of any one of the above embodiments and any one or more of the further embodiments herein, wherein the identified, marked, or stained intraocular structure(s) or membrane(s) within the patient's eye is a lens capsule.

In a further embodiment, the ophthalmic composition, or the method, of any one of the above embodiments and any one or more of the further embodiments herein, wherein the identified, marked, or stained intraocular structure(s) or membrane(s) within the patient's eye is a retinal membrane.

In a further embodiment, the ophthalmic composition, or the method, of any one of the above embodiments and any one or more of the further embodiments herein, wherein the identified, marked, or stained intraocular structure(s) or membrane(s) within the patient's eye is a corneal endothelial membrane.

In a further embodiment, the ophthalmic composition, or the method, of any one of the above embodiments and any one or more of the further embodiments herein, wherein the identified, marked, or stained intraocular structure(s) or membrane(s) within the patient's eye is a Descemet's membrane.

In a further embodiment, the ophthalmic composition, or the method, of any one of the above embodiments and any one or more of the further embodiments herein, wherein the Indigo Carmine of the ophthalmic composition identifies, marks, or stains a trabecular meshwork and a canal of Schlemm in the patient's eye.

In a further embodiment, the ophthalmic composition, or the method, of any one of the above embodiments and any one or more of the further embodiments herein, wherein the Indigo Carmine of the ophthalmic composition identifies, marks, or stains a canal of Schlemm more than a trabecular meshwork in the patient's eye.

In a further embodiment, the ophthalmic composition, or the method, of any one of the above embodiments and any one or more of the further embodiments herein, wherein the Indigo Carmine of the ophthalmic composition identifies, marks, or stains a trabecular meshwork less than a canal of Schlemm in the patient's eye.

In a further embodiment, the ophthalmic composition, or the method, of any one of the above embodiments and any one or more of the further embodiments herein, wherein the method facilitates diagnosis of the patient's eye.

In a further embodiment, the ophthalmic composition, or the method, of any one of the above embodiments and any one or more of the further embodiments herein, wherein the method facilitates diagnosis of the intraocular structure(s) or membrane(s) within the patient's eye.

In a further embodiment, the ophthalmic composition, or the method, of any one of the above embodiments and any one or more of the further embodiments herein, wherein the method facilitates an ocular surgeon's diagnosis of fluid flow and drainage of the patient's eye during the ocular surgery.

In a further embodiment, the ophthalmic composition, or the method, of any one of the above embodiments and any one or more of the further embodiments herein, wherein the method facilitates treatment of the patient's eye.

In a further embodiment, the ophthalmic composition, or the method, of any one of the above embodiments and any one or more of the further embodiments herein, wherein the method facilitates surgical treatment of the patient's eye.

In a further embodiment, the ophthalmic composition, or the method, of any one of the above embodiments and any one or more of the further embodiments herein, wherein the method facilitates surgical treatment of the identified intraocular structure(s) or membrane(s) within the eye.

In a further embodiment, the ophthalmic composition, or the method, of any one of the above embodiments and any one or more of the further embodiments herein, wherein the method facilitates surgical removal of the identified intraocular structure(s) or membrane(s) within the eye.

In a further embodiment, the ophthalmic composition, or the method, of any one of the above embodiments and any one or more of the further embodiments herein, wherein the method facilitates extracting a cataract and treating glaucoma.

In a further embodiment, the ophthalmic composition, or the method, of any one of the above embodiments and any one or more of the further embodiments herein, wherein the method further comprises introducing an ophthalmic device into the instilled eye.

In a further embodiment, the ophthalmic composition, or the method, of any one of the above embodiments and any one or more of the further embodiments herein, wherein the instilled ophthalmic composition facilitates accurate and/or precise inserting, placement, positioning, repositioning, lifting, and/or removal, of an ophthalmic device within the patient's eye.

In a further embodiment, the ophthalmic composition, or the method, of any one of the above embodiments and any one or more of the further embodiments herein, wherein the method facilitates accurate and/or precise inserting, placement, positioning, repositioning, lifting, and/or removal, of an ophthalmic device proximate the identified intraocular structure(s) or membrane(s) within the patient's eye.

In a further embodiment, the ophthalmic composition, or the method, of any one of the above embodiments and any one or more of the further embodiments herein, wherein the method facilitates accurate and/or precise inserting, placement, positioning, repositioning, lifting, and/or removal, of a plurality of ophthalmic devices within the Indigo Carmine instilled patient's eye.

In a further embodiment, the ophthalmic composition, or the method, of any one of the above embodiments and any one or more of the further embodiments herein, wherein the method facilitates accurate and/or precise inserting of an ophthalmic device proximate the identified intraocular structure(s) or membrane(s) within the patient's eye.

In a further embodiment, the ophthalmic composition, or the method, of any one of the above embodiments and any one or more of the further embodiments herein, wherein the method facilitates accurate and/or precise placement of an ophthalmic device proximate the identified intraocular structure(s) or membrane(s) within the patient's eye.

In a further embodiment, the ophthalmic composition, or the method, of any one of the above embodiments and any one or more of the further embodiments herein, wherein the method facilitates accurate and/or precise positioning of an ophthalmic device proximate the identified intraocular structure(s) or membrane(s) within the patient's eye.

In a further embodiment, the ophthalmic composition, or the method, of any one of the above embodiments and any one or more of the further embodiments herein, wherein the method facilitates accurate and/or precise repositioning of an ophthalmic device proximate the identified intraocular structure(s) or membrane(s) within the patient's eye.

In a further embodiment, the ophthalmic composition, or the method, of any one of the above embodiments and any one or more of the further embodiments herein, wherein the method facilitates accurate and/or precise removal of an ophthalmic device proximate the identified intraocular structure(s) or membrane(s) within the patient's eye.

In a further embodiment, the ophthalmic composition, or the method, of any one of the above embodiments and any one or more of the further embodiments herein, wherein the ophthalmic device is a stent.

In a further embodiment, the ophthalmic composition, or the method, of any one of the above embodiments and any one or more of the further embodiments herein, wherein the method facilitates an ocular surgeon's determination of the type of stent to utilize during the ocular surgery.

In a further embodiment, the ophthalmic composition, or the method, of any one of the above embodiments and any one or more of the further embodiments herein, wherein the method facilitates an ocular surgeon's placement of the stent during the ocular surgery.

In a further embodiment, the ophthalmic composition, or the method, of any one of the above embodiments and any one or more of the further embodiments herein, wherein the method facilitates an ocular surgeon's determination of the type of stent to utilize and the placement of the stent during the ocular surgery.

In a further embodiment, the ophthalmic composition, or the method, of any one of the above embodiments and any one or more of the further embodiments herein, wherein the ophthalmic device is a glaucoma stent.

In a further embodiment, the ophthalmic composition, or the method, of any one of the above embodiments and any one or more of the further embodiments herein, wherein the ophthalmic device is a suprachoroidal stent.

In a further embodiment, the ophthalmic composition, or the method, of any one of the above embodiments and any one or more of the further embodiments herein, wherein the ophthalmic device is an intraocular lens during cataract surgery.

In a further embodiment, the ophthalmic composition, or the method, of any one of the above embodiments and any one or more of the further embodiments herein, wherein the ophthalmic device is introduced proximate to canal of Schlemm of the patient's eye.

In a further embodiment, the ophthalmic composition, or the method, of any one of the above embodiments and any one or more of the further embodiments herein, wherein the ophthalmic device is inserted into the canal of Schlemm of the patient's eye.

In a further embodiment, the ophthalmic composition, or the method, of any one of the above embodiments and any one or more of the further embodiments herein, wherein the ophthalmic device is inserted into the suprachorodial space of the patient's eye.

In a further embodiment, the ophthalmic composition, or the method, of any one of the above embodiments and any one or more of the further embodiments herein, wherein the ophthalmic device is pre-treated with Indigo Carmine.

In a further embodiment, the ophthalmic composition, or the method, of any one of the above embodiments and any one or more of the further embodiments herein, wherein the ophthalmic device is pre-treated with Trypan Blue.

In a further embodiment, the ophthalmic composition, or the method, of any one of the above embodiments and any one or more of the further embodiments herein, wherein the method further comprises instilling an ophthalmic composition comprising Trypan Blue.

In a further embodiment, the ophthalmic composition, or the method, of any one of the above embodiments and any one or more of the further embodiments herein, wherein the instilled the ophthalmic composition comprises both Indigo Carmine and Trypan Blue.

In a further embodiment, the ophthalmic composition, or the method, of any one of the above embodiments and any one or more of the further embodiments herein, wherein intraocular structures or membranes of the instilled eye are identified, marked, or stained, by Indigo Carmine prior to extracting of the cataract.

In a further embodiment, the ophthalmic composition, or the method, of any one of the above embodiments and any one or more of the further embodiments herein, wherein intraocular structures or membranes of the instilled eye are identified, marked, or stained, by both Indigo Carmine and Trypan Blue prior to extracting of the cataract.

In a further embodiment, the ophthalmic composition, or the method, of any one of the above embodiments and any one or more of the further embodiments herein, wherein the surgical treatment of the glaucoma in said Indigo Carmine instilled eye comprises introducing an ophthalmic device into said eye.

In a further embodiment, the ophthalmic composition, or the method, of any one of the above embodiments and any one or more of the further embodiments herein, wherein the surgical treatment of the glaucoma in said Indigo Carmine instilled eye comprises: a) visually identifying an Indigo Carmine stained canal of Schlemm; and b) introducing an ophthalmic device into the patient's eye proximate the Indigo Carmine stained canal of Schlemm.

In a further embodiment, the ophthalmic composition, or the method, of any one of the above embodiments and any one or more of the further embodiments herein, wherein the Indigo Carmine containing ophthalmic composition and the Trypan Blue containing ophthalmic composition are co-instilled concurrently, co-instilled sequentially with instilling of the Indigo Carmine containing ophthalmic composition followed by the Trypan Blue containing ophthalmic composition, or co-instilled sequentially with instilling of the Trypan Blue containing ophthalmic composition followed by the Indigo Carmine containing ophthalmic composition.

In a further embodiment, the ophthalmic composition, or the method, of any one of the above embodiments and any one or more of the further embodiments herein, wherein the ophthalmic composition is instilled into the patient's eye over a period of time in the range of between 1 second to 2 minutes.

In a further embodiment, the ophthalmic composition, or the method, of any one of the above embodiments and any one or more of the further embodiments herein, wherein the ophthalmic composition is instilled into the patient's eye over a period of at least 10 seconds, at least 20 seconds, at least 30 seconds, at least 45 seconds, at least 1 minute, or at least 1.5 minutes.

In a further embodiment, the ophthalmic composition, or the method, of any one of the above embodiments and any one or more of the further embodiments herein, wherein the ophthalmic composition is instilled into the patient's eye over a period of time until the composition egresses from one or more channels in the patient's eye.

In a further embodiment, the ophthalmic composition, or the method, of any one of the above embodiments and any one or more of the further embodiments herein, wherein a plurality of the instillations of the ophthalmic composition is conducted over a period of time until at least 25%, at least 50%, at least 75%, at least 90%, or at least 95%, of the canal of Schlemm is visually identifiable.

In a further embodiment, the ophthalmic composition, or the method, of any one of the above embodiments and any one or more of the further embodiments herein, wherein the method results in reduced surgical manipulation, relative to an ocular surgery not using said ophthalmic composition.

In a further embodiment, the ophthalmic composition, or the method, of any one of the above embodiments and any one or more of the further embodiments herein, wherein the method results in reduced tissue manipulation, relative to an ocular surgery not using said ophthalmic composition.

In a further embodiment, the ophthalmic composition, or the method, of any one of the above embodiments and any one or more of the further embodiments herein, wherein the method results in less severe adverse side effects, relative to an ocular surgery not using said ophthalmic composition.

All publications, patents, and patent applications, mentioned in this specification are herein incorporated by reference in their entirety to the same extent as if each individual publication, patent, or patent application, was specifically and individually indicated to be incorporated by reference in its entirety.

It will be understood that the embodiments disclosed and defined in this specification extends to all alternative combinations of two or more of the individual features mentioned or evident from the text or drawings. All of these different combinations constitute various alternative aspects of the present disclosure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An ophthalmic composition, comprising:
   i) 0.001-0.04 wt. % Indigo Carmine, relative to the ophthalmic composition; and
   ii) 0.001-0.1 wt. % Trypan Blue, relative to the ophthalmic composition.

2. The ophthalmic composition of claim 1, wherein the ophthalmic composition further comprises at least one dye selected from the group consisting of: Brilliant Blue, Patent Blue, Indocyanine Green, and Fluorescein.

3. The ophthalmic composition of claim 1, wherein the ophthalmic composition further comprises one or more additional ophthalmically acceptable excipients and additives.

4. The ophthalmic composition of claim 1, wherein the ophthalmic composition further comprises an anti-oxidant compound.

5. The ophthalmic composition of claim 1, wherein the ophthalmic composition comprises an ophthalmic irrigation solution.

6. The ophthalmic composition of claim 1, wherein the ophthalmic composition is an aqueous composition.

7. The ophthalmic composition of claim 1, wherein the ophthalmic composition is an isotonic, aqueous solution having a pH between 6-8.

8. The ophthalmic composition of claim 1, wherein the ophthalmic composition comprises inorganic salts and/or organic salts selected from the group consisting of sodium chloride, potassium chloride, calcium chloride, magnesium chloride, sodium acetate, sodium phosphate, sodium monohydrogen phosphate, sodium dihydrogen phosphate, sodium bicarbonate, and sodium citrate.

9. The ophthalmic composition of claim 1, wherein the ophthalmic composition has an osmolality between 200-400 mosmol/kg.

10. The ophthalmic composition of claim 1, wherein the ophthalmic composition is an injectable ophthalmic formulation.

11. The ophthalmic composition of claim 1, wherein the ophthalmic composition comprises 0.004-0.04 wt. % Indigo Carmine, relative to the ophthalmic composition.

12. A method for identification of canal of Schlemm within an eye of a patient in need thereof, comprising instilling the ophthalmic composition of claim 1 into the patient's eye.

13. The method of claim 12, wherein said ophthalmic composition is instilled into the anterior chamber of the patient's eye.

14. A method of cataract extraction and treatment of glaucoma in an eye of a patient in need thereof, comprising:
   i) instilling the ophthalmic composition of claim 1 into the patient's eye;
   ii) surgically extracting the cataract of the instilled eye; and
   iii) surgically treating the glaucoma of the cataract extracted eye.

15. The method of claim 14, wherein the method includes an ocular surgery, or the ocular surgery is, selected from the group consisting of: glaucoma surgery, minimally invasive glaucoma surgery (MIGS), cataract surgery, retinal surgery, lens replacement surgery, surgery to treat ocular trauma, refractive lensectomy, corneal surgery, endothelial keratoplasty, Descemet's Membrane Endothelial Keratoplasty (DMEK), capsulorhexis, lamellar corneal transplantation, minimally invasive corneal procedure, corneal refractive procedure, small incision lenticule extraction (SMILE), Ab interno Canaloplasty (ABiC), Ab externo Canaloplasty (ABeC), retinal procedures, and ocular surface diagnostic technique.

16. The method of claim 15, wherein the retinal procedure comprises removal of epiretinal membranes.

17. The method of claim 14, wherein the method identifies, marks, or stains an intraocular structure(s) or membrane(s) within the patient's eye in a visually identifiable manner.

18. The method of claim 17, wherein the identified, marked, or stained intraocular structure(s) or membrane(s) within the patient's eye is selected from a group consisting of: a fine vessel, an aqueous vein, an episcleral vein, a collector channel, a collector channel/aqueous/episcleral vein system, an aqueous drainage system, a conjunctival venous system, a deep scleral plexus, a deep scleral plexus visually identifiable once a conjunctiva is reflected away, a trabecular meshwork, a canal of Schlemm, a suprachoroidal space, a scleral spur, anterior capsule of a crystalline lens, cornea, lens capsule, a retinal membrane, a corneal endothelial membrane, and Descemet's membrane.

19. The method of claim 17, wherein the identified, marked, or stained intraocular structure(s) or membrane(s) within the patient's eye is conventional drainage system of said eye.

20. The method of claim 14, wherein the method further comprises introducing an ophthalmic device into the instilled eye.

21. The method of claim 20, wherein the ophthalmic device is introduced proximate to canal of Schlemm of the patient's eye or is inserted into the canal of Schlemm of the patient's eye.

22. The method of claim 20, wherein the ophthalmic device is a stent.

23. The method of claim 14, wherein the instilled ophthalmic composition facilitates accurate and/or precise inserting, placement, positioning, repositioning, lifting, and/or removal, of an ophthalmic device within the patient's eye.

24. The method of claim 14, wherein said ophthalmic composition is instilled into the anterior chamber of the patient's eye.

* * * * *